(12) United States Patent
Chen et al.

(10) Patent No.: US 6,251,599 B1
(45) Date of Patent: Jun. 26, 2001

(54) STABILIZED NUCLEIC ACID COMPOSITIONS AND METHODS OF PREPARATION AND USE THEREOF

(75) Inventors: Xian Chen; Chenglie Ma, both of San Diego; Mark J. D'Andrea, Carlsbad, all of CA (US)

(73) Assignee: Selective Genetics, Inc., San Diego, CA (US)

( * ) Notice: Subject to any disclaimer, the term of this patent is extended or adjusted under 35 U.S.C. 154(b) by 0 days.

(21) Appl. No.: 09/187,727

(22) Filed: Nov. 6, 1998

(51) Int. Cl.[7] .................................................... C12Q 1/68
(52) U.S. Cl. ........................ 435/6; 536/23.1; 536/23.3; 536/23.4; 536/23.5; 514/44
(58) Field of Search ............................... 435/6; 536/23.3, 536/23.1, 23.4, 23.5; 514/44

(56) References Cited

U.S. PATENT DOCUMENTS

| 5,783,567 | 7/1998 | Hedley et al. | 514/44 |
| 5,811,406 | 9/1998 | Szoka, Jr. et al. | 514/44 |

FOREIGN PATENT DOCUMENTS

WO 96/37194  11/1996 (WO).
WO 96/40067  12/1996 (WO).
WO 96/40265  12/1996 (WO).

OTHER PUBLICATIONS

Sosnowski et al., "Targeting DNA to Cells with Basic Fibroblast Growth Factor (FGF2)," *The Journal of Biological Chemistry* 271(52): 33647–33653, 1996.

Talsma et al., "Stabilization of Gene Delivery Systems by Freeze–Drying," *International Journal of Pharmaceutics* 157: 233–238, 1997.

Kim et al., "The Physical State of Mannitol after Freeze–Drying: Effects of Mannitol Concentration, Freezing Rate, and a Noncrystallizing Cosolute," *Journal of Pharmaceutical Sciences* 87(8): 931–935, 1998.

Perales et al., "An evaluation of receptor–mediated gene transfer using synthetic DNA–ligand complexes," *Eur. J. Biochem.* 226: 255–266, 1994.

*Primary Examiner*—Scott W. Houtteman
(74) *Attorney, Agent, or Firm*—Seed Intellectual Property Law Group PLLC

(57) ABSTRACT

Preparations of nucleic acid condensates and compositions containing such condensates are provided. The nucleic acid condensates are in the form of small particles that are stable when subjected to destabilizing conditions such as lyophilizing, freeze-thawing, and prolonged liquid storage. These compositions may be used to deliver nucleic acid to cells.

82 Claims, 9 Drawing Sheets tre: trehalose: suc: sucrose, man: D-mannitol

M: mannitol;   S: sucrose   T: trehalose   G: glycine

STABILIZED NUCLEIC ACID COMPOSITIONS AND METHODS OF PREPARATION AND USE THEREOF

TECHNICAL FIELD

The present invention relates generally to compositions that are useful in biological applications involving nucleic acids. In one embodiment, the present invention relates to stabilized nucleic acid-polycation condensates for delivery of genes to cells for the purpose of altering the function, gene expression, or viability of the cells.

BACKGROUND

The ability to introduce nucleic acid into cells is the cornerstone of many molecular biology techniques and their pharmaceutical applications. Many different delivery systems have been developed to introduce exogenous DNA into cells. These include viruses, liposomes, electroporation, cell fusion, microinjection and salt precipitation. (See, e.g., Sambrook et al., *Molecular Cloning, a Laboratory Manual*, Cold Spring Harbor Laboratory Press, Cold Spring Harbor, N.Y., 1989.) Although virus proteins and particles can provide efficient means of introducing exogenous DNA into target cells, problems associated with immunogenicity and potential infection have led to the production of synthetic delivery vehicles, such as cationic liposomes. Although many synthetic delivery systems may involve nonspecific cellular uptake, a variety of cell-specific delivery systems are also available.

Synthetic delivery vehicles for introduction of heterologous DNA into specific cells are architecturally complicated and often unstable under various preparatory and/or storage conditions. Not only must the DNA be maintained in a condition that ensures its structural integrity and functionality, the delivery vehicle itself, if attached to a ligand, should maintain the capability of being recognized and internalized by the target cell. It is often the case that a mechanism capable of achieving one of these goals has a negative effect on the other. For example, polycation-nucleic acid condensates in the form of compact particles show great promise as gene delivery vehicles. However, the stability of such condensates in the liquid and frozen state is limited due to their propensity to aggregate and fall out of solution.

Therefore, there exists a need in the art for nucleic acid molecule compositions which maintain their stability under a variety of different conditions that have been shown to destabilize various prior compositions. The present invention fulfills this need, while further providing other related advantages.

SUMMARY OF THE INVENTION

In one aspect, the invention provides a composition comprising a nucleic acid condensed with a polycation in a liquid medium, thereby forming a particle, wherein the particle increases in size by less than one-fold during storage in the liquid medium for one week at about 2° C. to about 8° C. In certain embodiments the composition further comprises at least one excipient selected from a zwitterion, an amorphous cryoprotectant, a crystalline bulking agent, and mixtures thereof. In other embodiments the composition further comprises a ligand. In yet another embodiment the ligand is a polypeptide reactive with a cell growth factor receptor.

In another aspect, the invention provides a condensate comprising a nucleic acid, a polycation, and at least one excipient selected from a zwitterion, an amorphous cryoprotectant, a crystalline bulking agent, and mixtures thereof. In one embodiment, the excipient comprises a zwitterion, an amorphous cryoprotectant, and/or a crystalline bulking agent. In other embodiments the excipient comprises a cryoprotectant and a crystalline bulking agent. In yet other embodiments the condensate comprises a mixture of a first zwitterion and a second zwitterion.

In a further embodiment, the condensate has a nucleic acid concentration of less than about 20 mg/ml. In yet another embodiment the condensate has a polycation concentration of less than about 40 mg/ml. In additional embodiments the condensate comprises a nucleic acid:polycation charge ratio of less than 1:1. In other embodiments the condensate is a particle, and the particle increases in size less than one-fold during storage in a liquid medium for one week at about 2° C. to about 8° C. In other various embodiments the composition further comprises a ligand.

In yet another aspect, the invention provides a lyophile prepared by the process comprising the steps: (a) combining water, nucleic acid, polycation, and an excipient, thereby forming a plurality of particles; and (b) removing water from (a). In one embodiment the excipient is selected from a zwitterion, an amorphous cryoprotectant, a crystalline bulking agent, and mixtures thereof. In another embodiment substantially all of the water is removed from the lyophile. In the various embodiments the excipient may comprise multiple components including multiple zwitterions. In preferred embodiments, the polycation is selected from a polyamino acid, protamine, histone, and a polymer. In yet another embodiment, the lyophile is reconstituted in a liquid medium to provide particles, wherein the particles increase in size by less than one-fold as compared to particles before lyophilization. In a further embodiment, the lyophile comprises a ligand.

In a further aspect, the present invention provides a composition comprising a nucleic acid, a polycation, and an excipient, and further comprising a ligand covalently attached to at least one of these components. In one embodiment the ligand is covalently conjugated to the polycation forming a polycation-ligand conjugate. In another embodiment the ratio of the polycation-ligand conjugate to nucleic acid is less than about 5:1 (w:w). In yet a further embodiment, the ligand is a polypeptide reactive with a cell growth factor receptor. In a preferred embodiment the ligand is a polypeptide reactive with a fibroblast growth factor (FGF) receptor. In yet another embodiment the excipient is selected from a zwitterion, an amorphous cryoprotectant, a crystalline bulking agent, and mixtures thereof. In another embodiment the composition forms a plurality of particles wherein the particles increase in size by less than one-fold during storage in a liquid medium for one week at about 2° C. to about 8° C.

In yet another aspect, the present invention provides a method of preparing condensed nucleic acid comprising the steps of: (a) admixing a nucleic acid and a polycation in a liquid medium to form an admixture; (b) incubating the admixture under conditions in which the nucleic acid and the polycation condense to form a plurality of particles; (c) lyophilizing the admixture to remove the liquid medium thereby producing a lyophile comprising particles; and (d) reconstituting the lyophile with a predetermined volume of a reconstituting medium to form a reconstituted composition comprising a plurality of particles that increase in size less than one-fold during storage in the reconstituting liquid for one week at about 2° C. to about 8° C.

In one embodiment, the average size of the particles in the reconstituted composition of step (d) is less than twice the average particle size of the particles in step (b). In a further embodiment, the concentration of particles in the reconstituted composition of step (d) is greater than the concentration of particles in the composition prepared in step (b). In yet another embodiment, the method further comprises the additional step of admixing an amorphous cryoprotectant into the liquid medium before step (c). In further embodiments, various excipients selected from a zwitterion, an amorphous cryoprotectant, crystalline bulking agent, and mixtures thereof are added before step (c). In additional embodiments the polycation has a ligand attached thereto. In yet another embodiment, the particles in the reconstituted composition have a hydrodynamic diameter of less than about 200 nm. In still another embodiment, the average size of the particles in the reconstituted composition of step (d) increases less than one fold during storage at about 2° C. to about 8° C. for one week.

In still another aspect, the present invention provides a composition for the delivery of a nucleic acid to a mammalian cell prepared by the aforementioned method.

DETAILED DESCRIPTION

Figure 1:
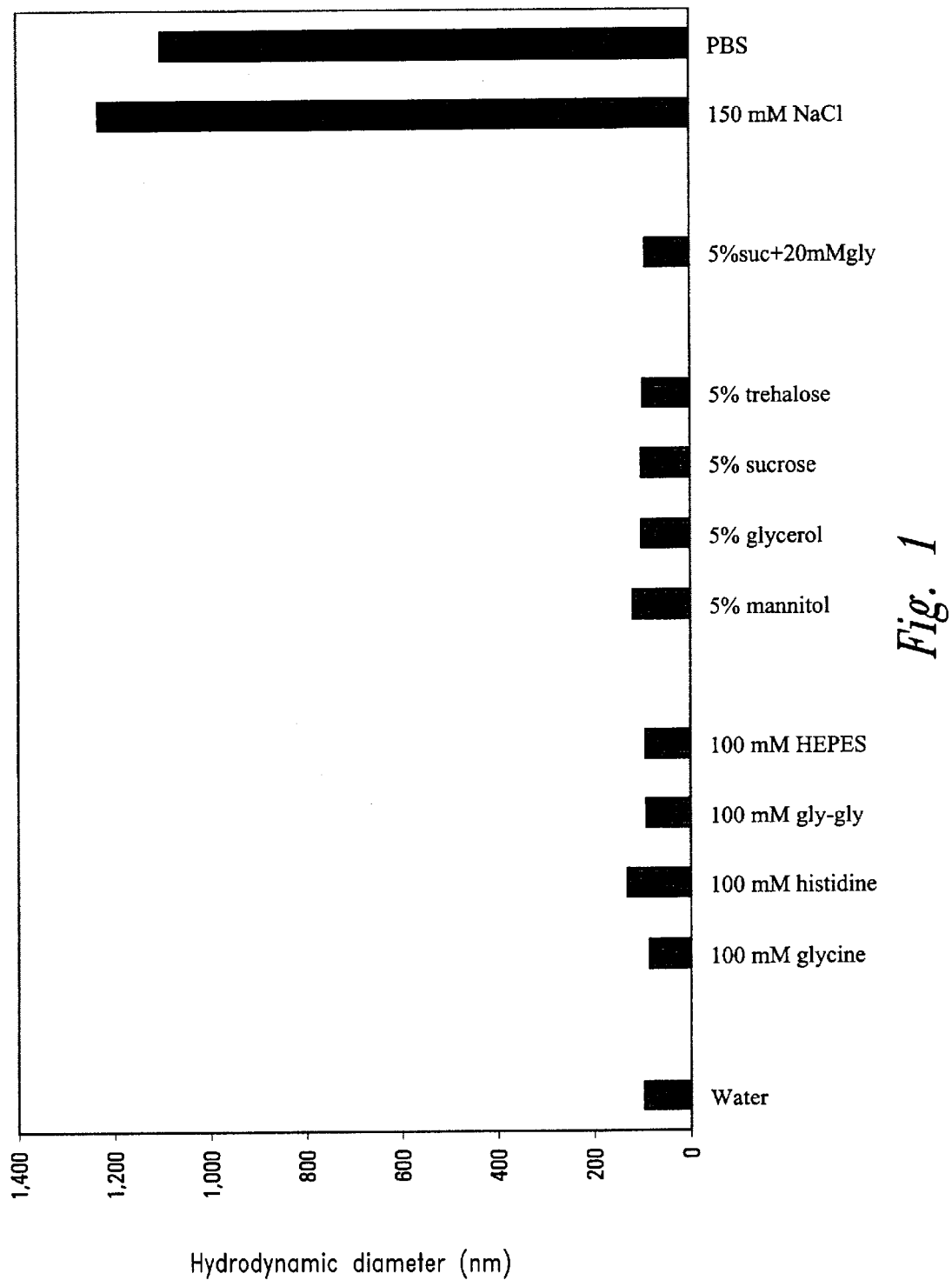
FIG. 1 is a graph depicting the effects of different excipients on particle size as described in Example 1.

The present invention relates to stabilized nucleic acid compositions that are useful for a variety of applications including the delivery of nucleic acids, typically DNA, to cells. In various embodiments, the compositions are in the form of condensed nucleic acid-containing particles that may be targeted for delivery to a particular cell or tissue type by using a ligand that is specific for a cell surface receptor. Upon binding to an appropriate receptor, the complex can be internalized by the cell and processed through the cell (generally trafficking via the endosomal compartment where at least a portion of the complex may be cleaved).

Particles comprising polycation-nucleic acid condensates are sensitive to certain conditions during the preparation and storage process and may thus become unstable. Typically such instability results in aggregation due to the presence of salts, pH and temperature fluctuations, mechanical agitation, freezing and thawing, and freeze-drying and reconstituting. However, the particles of the present invention are superior in that they remain in solution under a variety of such conditions.

The most significant and evident form of instability is represented by particle size increases due to aggregation of smaller particles, which almost always leads to visible precipitation. Such a change in visible morphology is not only aesthetically undesirable, but it often correlates with a loss or change of gene transfer efficacy. For example, the diameter of capillaries and endothelial pores may restrict passage of large DNA-polycation condensates. In addition, it is generally accepted that small DNA-containing particles (e.g., particles of approximately 20–100 nm diameter) facilitate endocytosis by the targeted tissue and permit entry through nuclear pores for efficient transgene expression. (Perales et al., *Eur. J. Biochem* 226:255–266 (1994)).

Further, in one embodiment, unlike liposomal nucleic acid delivery vehicles, the compositions of the present invention generally contain less than about 1% (w/w) lipid, and in other embodiments less than about 0.1% (w/w) lipid. In addition, in other embodiments, unlike salt-induced nucleic acid precipitates, the compositions of the present invention can contain less than about 1% (w/v) salt, and in other embodiments may contain less than about 0.1% (w/v) salt.

DEFINITIONS

Prior to setting forth further details of the present invention, it may be helpful to an understanding thereof to set forth definitions of certain terms that will be used hereinafter.

As used herein, the term "nucleic acid(s)" includes duplex DNA, single-stranded DNA, RNA in any form, including triplex, duplex or single-stranded RNA, anti-sense DNA or antisense RNA, polynucleotides, oligonucleotides, single nucleotides, chimeras, and derivatives and analogues thereof. It is intended that where DNA is exemplified herein, other types of nucleic acids would also be suitable. Nucleic acids may be composed of the well-known deoxyribonucleotides and ribonucleotides composed of the bases adenosine, cytosine, guanine, thymidine, and uridine, or may be composed of analogues or derivatives of these bases. As well, various other oligonucleotide derivatives with non-phosphate backbones or phosphate-derivative backbones may be used. For example, because normal phosphodiester oligonucleotides (referred to as PO oligonucleotides) are sensitive to DNA- and RNA-specific nucleases, oligonucleotides resistant to cleavage, such as those in which the phosphate group has been altered to a phosphotriester, methylphosphonate, or phosphorothioate may be used (see U.S. Pat. No. 5,218,088).

As used herein, "operative linkage" or "operative association" of DNA to regulatory and/or effector nucleotide sequences refers to a functional relationship between the DNA and the nucleotide sequences. For example, an operative linkage of a cytocide encoding DNA to a promoter refers to the physical and functional relationship between the DNA and the promoter, such that transcription of the DNA is initiated from the promoter by an RNA polymerase that specifically recognizes, binds to and transcribes the DNA.

As used herein, the terms "therapeutic nucleic acid," "therapeutic sequence," or "therapeutic gene" describe any nucleic acid molecule used in the context of the invention that effects a treatment, generally by modifying gene transcription or by producing a gene product which itself ameliorates the specific condition of the patient. Such terms, which may be used interchangeably herein, describe any nucleic acid that is taken up into a cell, either directly or indirectly, and which affects cellular metabolism, growth, activity, viability or some other property or characteristic of a cell. Such therapeutic nucleic acids include, without limitation, replacement genes, antisense oligonucleotides, ribozymes, deoxyribozymes, pro-drug-encoding agents, and cytocide-encoding agents. The product of a cytocide-encoding agent may be cytotoxic (i.e., it results in cell death or renders a cell susceptible to cell death), or it may be a nontoxic form that is capable of being converted to a toxic form by an activator within the target cell or an exogenously supplied activator. It includes, but is not limited to, the following types of nucleic acids: nucleic acids encoding a protein, antisense RNA, DNA intended to form triplex molecules, protein binding nucleic acids, and small nucleotide molecules. A therapeutic nucleic acid may be used to effect genetic therapy by serving as a replacement for a defective gene, or by encoding a therapeutic product, such as a tumor-suppressing agent, prodrug, proliferation enhancer, wound healing agent, or cytocide, to name a few examples. The therapeutic nucleic acid may contain all or a portion of a gene and may function by recombining with DNA already present in a cell, thereby replacing or complementing a defective portion of a gene. It may also encode a portion of a protein and exert its effect by virtue of co-suppression of a gene product.

As used herein, "polycation" refers to a molecule with a multiplicity of positive charges that is capable of electrostatically interacting with a nucleic acid molecule to condense the latter into particulate form. Such molecules are typically polycationic polymers, including polycationic peptides or proteins, polycationic carbohydrates, non-peptide polyamines and polycationic synthetic polymers. Examples of polycationic peptides include, without limitation, polylysine, polyornithine, protamines, chitosan and histones.

As used herein, the term "polypeptide or protein reactive with a cell receptor" refers to any protein that specifically binds to the receptor of interest. For example, the term "polypeptide reactive with an FGF receptor" refers to any polypeptide that specifically interacts with an FGF receptor, preferably the high-affinity FGF receptor. Proteins or polypeptides reactive with an FGF receptor are also called "FGF proteins" or "FGF polypeptides," respectively.

As used herein, a "prodrug" is a compound that metabolizes or otherwise converts an inactive, nontoxic compound to an active form of the compound—e.g. biologically, pharmaceutically, or therapeutically active. A prodrug may also be a pharmaceutically inactive compound that is modified upon administration to yield an active compound through metabolic or other processes. The prodrug may alter the metabolic stability or the transport characteristics of a drug, mask side effects or toxicity, improve or alter other characteristics or properties of a drug. By virtue of knowledge of pharmacodynamic processes and drug metabolism in vivo, those of skill in this art, once a pharmaceutically active compound is known, can design inactive forms of the compound (see, e.g., Nogrady, *Medicinal Chemistry A Biochemical Approach*, Oxford University Press, New York, pages 388–392, 1985).

As used herein, "protein" refers to any native or non-native protein, as well as modified forms that have amino acid substitutions, deletions, insertions or additions, and also includes polypeptides, oligopeptides, protein analogues, and peptidomimetics, any of which may be in either D, L or D-L conformation.

As used herein, the term "ligand" refers to a compound (or a portion of a compound) that binds to a cell surface receptor, which in turn refers to the ability of a ligand to specifically recognize and detectably bind to such receptors, as assayed by standard in vitro assays. Receptor binding assays from which a binding constant can be determined are well-known in the art for a variety of receptor types. For example, a procedure to measure the binding of a VEGF conjugate, VEGF monomer, or VEGF dimer to a VEGF receptor on a vascular endothelial cell is described in Moscatelli, J. *Cell Physiol.* 131:123–130 (1987).

As used herein, the term "ligand-polycation conjugate" or "polycation-ligand conjugate" refers to a composition that contains at least one ligand for a cell surface receptor and at least one polycation. Preferably, the ligand and polycation of the conjugate are covalently linked, either directly or through a linking group. The covalent linkage is formed by chemical coupling methods. Alternatively, the ligand-polycation conjugate may be a fusion protein formed by the recombinant expression of chimeric DNA molecules. In a further alternative, the ligand-polycation conjugate may be electrostatically coupled. In an even further alternative, the ligand and polycation are part of the same composition, but are not attached to each other. Instead, the ligand is coupled to another component of the composition. For example, the ligand may be coupled to either the nucleic acid or an excipient.

As used herein, the term "condensate" refers to the condensation product of the reaction between polycation and at least one nucleic acid molecule. Whereas the term "complexation" refers generally to the electrostatic interaction of the nucleic acid and the polycation, the term "condensation" refers to the compacting of such complexes into small particles.

A "lyophile" as used herein, refers to the end product of a lyophilization or freeze-drying procedure. Such a composition is substantially free of aqueous components.

As used herein, the term "excipient" refers to any additive useful in the present invention, such that the additive increases the stability of the condensate and/or provides for pharmaceutically acceptable compositions. Exemplary excipients in this regard are zwitterions, amorphous cryprotectants, and crystalline bulking agents.

As used herein, the term "zwitterion" refers to a molecule that contains both positive and negative charges. Such molecules contain multiple ionizing groups and contain groups of both acidic and basic pKa values. Such molecules are typically termed ampholytes. However, ampholytes in a state such that the molecule contains both positive and negative charges is called a zwitterion.

As used herein, the term "amorphous cryoprotectant" refers to a compound which, when included in the formulations of the present invention during freezing or lyophilization under given conditions, does not form crystals. It is specifically intended that compounds that are known to form crystals under certain lyophilization conditions but not under others are included within the term "amorphous cryoprotectant", so long as they remain amorphous under the specific freezing or lyophilization conditions to which they are subjected.

As used herein, "crystalline bulking agent" refers to a compound which, when included in the formulations of the present invention during freezing or lyophilization under given conditions, forms crystals. It is specifically intended that compounds that are known to form crystals under certain lyophilization conditions but not under others are included within the term "crystalline bulking agent", so long as they crystallize under the specific freezing or lyophilization conditions to which they are subjected.

Amorphous cryoprotectants, crystalline bulking agents, and methods of determining the same are known and available in the art. The following articles, incorporated herein by reference, provide a basic teaching in this regard: Osterberg et al., *Pharm Res* 14(7):892–898, 1997; Oliyai et al., *Pharm Res* 11(6):901–908, 1994; Corveleyn et al., *Pharm Res* 13(l):146–150, 1996; Kim et al., *J. Pharm Sciences* 87(8):931–935, 1998; Martini et al., *PDA J. Pharm Sci Tech* 51(2):62–67, 1997; Martini et al., *STP Pharma Sci.* 7(5):377–381, 1997; and Orizio et al., *Boll. Chim. Farm.* 132(9):368–374, 1993.

As used herein, "biological activity" or "bioactivity" refers to the activities of a molecule or compound or to the physiological responses that result upon in vivo or in vitro administration of a compound, composition or other mixture. Such biological activity may be defined with reference to particular in vivo or in vitro activities as measured in a defined assay. For example, within the context of this invention, the biological activity of FGF, or fragments of FGF, may refer to the ability of FGF to bind to cells bearing FGF receptors and may also refer to the ability of the FGF to facilitate internalization of a targeted agent. One exemplary method of assessing biological activity is done in vitro by linking the FGF to a cytotoxic agent, such as saporin, contacting cells bearing FGF receptors (e.g., fibroblasts) with the conjugate, and assessing cell proliferation or growth. In vivo activity may be determined using recognized animal models, such as the mouse xenograft model for anti-tumor activity (see, e.g., Beitz et al., *Cancer Research* 52:227–230, 1992; Houghton et al., *Cancer Res.* 42:535–539, 1982; Bogden et al., *Cancer* (Philadelphia) 48:10–20, 1981; Hoogenhout et al., *Int. J. Radiat. Oncol., Biol. Phys.* 9:871–879, 1983; Stastny et al., *Cancer Res.* 53:5740–5744, 1993).

As used herein, the "biological activity of a nucleic acid," such as DNA encoding a cytocide, a prodrug, a therapeutic molecule, or another nucleic acid molecule refers to the ability of the nucleic acid or encoded product to have a discernible or detectable effect upon or within cells. Such biological activity may be assayed by any method known to those of skill in the art including, but not limited to, in vitro and/or in vivo assays that assess efficacy by measuring the effect on cell proliferation or on protein synthesis. Further, reporter gene activity in this regard refers to the ability of the reporter gene to express a detectable product such as B-gal or Green Fluorescent Protein (GFP).

As used herein, amino acids that occur in the various amino acid sequences appearing herein are identified according to their well-known three-letter or one-letter abbreviations. Additionally, the nucleotides, which occur in various RNA and DNA fragments, are designated with the standard single-letter designations used routinely in the art. However, use of such abbreviations does not imply that only native, unmodified amino acids or nucleotides are intended.

As used herein, "stable" refers to the ability of condensed particles to maintain a hydrodynamic volume such that the size of the nucleic acid containing particle does not increase greater than one-fold following storage at one week at about 2° C. to about 8° C.

As used herein, "biological buffer" refers to buffers that are zwitterionic and that have a buffering capacity at 37° C. within biologically acceptable pH ranges of about 6 to about 9.

COMPOSITION COMPONENTS

The preferred formulations of the present invention comprise nucleic acid:nucleic acid-binding molecule complexes that condense by our theory via electrostatic interaction of the nucleic acid-binding molecule with the nucleic acid, into stable particles. As such, the principle components of the compositions of the present invention include nucleic acids, nucleic acid-binding molecules, and stability enhancing excipients.

A. NUCLEIC ACID-BINDING MOLECULES

The nucleic acid-binding molecules that are useful in the present invention, while not wanting to be bound by a specific theory, tend to form electrostatic bonds with the negatively charged nucleic acid. This causes condensation of the nucleic acid into tightly compacted structures that, under appropriate conditions, remain stable in solution. In many preferred embodiments, the nucleic acid-binding molecule is a polycation. While polycations are described herein as exemplary, it should be appreciated that other molecules that share the desired characteristics—e.g., the ability to condense nucleic acids—are within the scope of the invention and may readily be substituted for polycations.

The polycation can be any of a variety of compounds possessing multiple positive charges. The polycation may be a polymer, which can take the form of a homopolymer of a single repeating unit or a block or random copolymer of two or more different repeating units. Examples of suitable classes of polycations include, without limitation, protamines, histones, polyamines, synthetic polypeptides and non-peptide, natural or synthetic polymers. The polycation may be present alone, or as a mixture of two or more different polycations.

Nucleic acid-binding molecules, of which polycations are exemplary, can be isolated from nature or synthetically produced using chemical means or recombinant methods. In addition, modifications to the molecular size and repeating unit sequence can easily be made to the polymeric polycations to optimize binding characteristics to the desired nucleic acid. The polycations described below are representative examples and are not intended to be limiting. Other types of polycations may be equally suitable if they are capable of electrostatic interaction with nucleic acids in a similar manner.

Nucleic acid condensation reactions with polycations are described in further detail below. However, it should be recognized that the ratio of polycation(s) to nucleic acid, as well as the overall charge and charge distribution of the polycation(s) can easily be selected using well known principles to optimize the characteristics of the nucleic acid condensate.

In one embodiment the nucleic acid:polycation charge ratio is less than 1:1 and in other embodiments this charge ratio is between about 1:1 to about 1:2. While higher charge ratios may be utilized, these can result in less efficient condensation of the nucleic acid.

Nucleic acid-binding molecules may also vary in length and still maintain their usefulness as disclosed herein. Those of skill in the art may readily determine the optimal length of an nucleic acid-binding molecule and will appreciate that the size and charge of the nucleic acid that requires condensing is generally relevant— if not determinative—of the length, charge and nature of the nucleic acid-binding molecule selected for use in a conjugate according to the present invention. Thus, in various applications, a nucleic acid-binding molecule (e.g., a polycation) may contain up to 50–100 amino acid residues, whereas in other applications, a nucleic acid-binding molecule of up to 100 residues, or up to 150 residues, or even more than 150 residues, may be useful as disclosed herein. As noted previously, the optimal length, charge, and composition of an nucleic acid-binding molecule may readily be determined by one of skill in the art for use with a particular nucleic acid. The preferred concentration of the nucleic acid-binding molecule is such as to impart a net positive charge to nucleic acid:nucleic acid-binding molecule complex, thereby resulting in compaction of nucleic acid into a stable small particle.

1. Synthetic Polypeptides

Synthetic polypeptides, or "polyamino acids", are particularly well-suited in the practice of the present invention because they provide for homogeneous preparations of nucleic acid condensates. Preferably, the synthetic polypeptide is a homologous polymer of one of the positively charged (i.e., basic) amino acids such as lysine or arginine, or a heterologous polymer of two or more positively charged amino acids. In addition, the polymer may consist of one or more positively charged nonstandard amino acids such as ornithine, 5-hydroxylysine and the like. Further, the polymer may consist of a mixture of positive, neutral and negative amino acids so long as the net charge is positive. In various embodiments the polycation is poly-D-lysine, poly-L-lysine, or poly-DL-lysine. Poly-D-lysine is particularly preferred in the practice of the present invention. Such polyamino acids may contain from at least 5 amino acid residues, and preferably from about 20 to about 150 more amino acid residues, preferably from about 50 to about 150 amino acid residues, and even more preferably from about 50 to about 100 amino acid residues.

2. Protamines

Also suitable for use are protamines. Protamines are a specialized class of strongly basic polypeptides which contain multiple positively charged amino acids, usually arginine. (See, e.g., James A. Hoffman, et al., *Protein Expression and Purification* 1:123–133 (1990)). For example, protamine sulfate purified from chum salmon (also referred to as salmine) is a small cationic protein that consists of a single polypeptide chain of 32 amino acids, of which 21 are arginine.

3. Histones

This class of compounds includes small DNA-binding proteins which are usually associated with chromatin and have a high proportion of positively charged amino acids, such as lysine and arginine. For example, histones H1 and H5 have been described as particularly efficient condensers of DNA. Hsing, M. W. and Cole, R. D., *Proc. Natl. Acad. Sci. USA* 74:4852–4856 (1977), and Garcia-Rammirez, M. and Subirana, J. *Biopolymers* 34:285–292 (1994).

4. Non-Peptide Polymers

Many natural and synthetic organic polymers bearing multiple charges, such as polyethyleneimine and chitosan, are also useful in the practice of the present invention. Polyamines such as spermine and spermidine that are derived from methionine and ornithine are particularly useful. These compounds play a role in the packaging of DNA during certain stages in cellular replication, and may also be useful herein as polycations.

5. Small Polycationic Molecules

Also suitable are many small polycationic compounds of charge 3+ or greater (Ma, J. et al. *Biopolymers* 35:211–216, 1995). Included within this class are the naturally occurring polyamines, noted above, spermidine, spermine, and polybrene, as well as cobalt hexamine and the like.

B. NUCLEIC ACIDS

Any nucleic acid may be incorporated into the compositions of the present invention. As noted, the therapeutic nucleic acid may encode a prodrug which activates an otherwise inactive agent within the target cell into an active one. Other suitable nucleic acids encode gene products that render a cell susceptible to toxic agents. Such products include tumor necrosis factor, viral proteins, and channel proteins that transport drugs, to name a few examples. Alternatively, the nucleic acids may encode a gene product that renders a cell resistant to toxic or infectious agents.

Further, nucleic acids can be linear or circular nucleic acids, or may adopt some other tertiary configuration. In various embodiments, the nucleic acid is a double-stranded nucleic acid (e.g., DNA) in the form of small plasmids. Preferably, the DNA sequence contains mammalian-preferred codons—that is, codons optimized for expression in mammalian cells. Preferred codon usage has been established for many targeted agents and is exemplified in *Current Protocols in Molecular Biology*, infra, and Zhang et al. (*Gene* 105:61, 1991) for mammals, yeast, Drosophila, *E. coli*, and primates.

The nucleic acids, preferably DNA, may be isolated, synthesized or obtained from commercial sources or prepared as described herein. DNA may be prepared synthetically based on the amino acid or may be isolated using methods known to those of skill in the art, such as PCR, probe hybridization of libraries, and the like, or obtained from commercial or other sources. For example, nucleic acids (including oligonucleotides) for use as described herein can be synthesized by any method known to those of skill in this art (see, e.g., WO 93/01286, U.S. application Ser. No. 07/723,454; U.S. Pat. No. 5,218,088; U.S. Pat. No. 5,175,269; U.S. Pat. No. 5,109,124).

Condensates including nucleic acid molecules encoding therapeutic agents or reporter genes are two of the preferred variants of the present invention. Therapeutic nucleic acids of the present invention may be used in the context of "positive" or "negative" gene therapy, depending on the biological effect being sought. Further, reporter genes may be used to investigate a variety of concerns, including tissue-specific expression, and as potential imaging or tagging agents.

The replacement of all or a portion of a defective or nonfunctional gene with one that produces the desired gene product is also considered "positive" gene therapy. Positive gene therapy typically entails replacing a dysfunctional or nonfunctional regulatory sequence or a sequence that encodes a structural protein. Similarly, "negative" gene therapy is encompassed by the present invention as well. Thus, therapeutic nucleic acids of the present invention may encode products that reduce or halt hyperproliferative diseases, tumor formation and growth, metastasis, and the like, to name a few examples.

1. Gene Replacement or Enhancement

Nucleic acids for delivery of "positive" gene therapy also include DNA molecules that encode proteins to replace defective genes or provide factors to combat certain diseases or syndromes. Many genetic defects are caused by a mutation in a single gene. Introduction of the wild-type gene will serve to alleviate the deficiency or genetic abnormality. Such genes include HPRT, adenosine deaminase, LDL receptor, Factor IX, Factor VIII, growth hormone, von Willebrand factor, PTH (parathyroid hormone), M-CSF, TGF-β, PDGF, VEGF, FGF, IGF, BMP (bone morphogenic protein), collagen type VII, fibrillin, insulin, cystic fibrosis transmembrane conductance regulator, adenosine deaminase, and the like.

For example, in ischemia, endothelial and smooth muscle cells fail to proliferate. A construct that expresses FGF, can be used to combat effects of ischemia. In such a case, the FGF gene with a leader sequence to promote secretion is preferable. As well, the FGF gene is preferably driven by a constitutive promoter.

In addition, certain angiogenic diseases suffer from a paucity of angiogenic factor and thus may be deficient in microvessels. Certain aspects of reproduction, such as ovulation, repair of the uterus after menstruation, and placenta development depend on angiogenesis. For reproductive disorders with underlying angiogenic dysfunction, a construct that expresses FGF, VEGF, or other angiogenic factors, may be beneficial.

Cytokine immunotherapy is a modification of immunogene therapy and involves the administration of tumor cell vaccines that are genetically modified ex vivo or in vivo to express various cytokine genes. In animal tumor models, cytokine gene transfer resulted in significant antitumor immune response (Fearon, et al., *Cell* 60:387–403, 1990; Wantanabe, et al., *Proc. Nat. Acad Sci. USA,* 86:9456–9460, 1989). Thus, in the present invention, the condensates are used to deliver DNA encoding a cytokine, such as IL-12, IL-10, IL-2, GM-CSF, INF-γ, or an MHC gene, such as HLA-B7. Delivery of these genes will modulate the immune system, increasing the potential for host antitumor immunity. Alternatively, DNA encoding costimulatory molecules, such as B7.1 and B7.2, ligands for CD28 and CTLA-4 respectively, can also be delivered to enhance T cell mediated immunity. These genes can be co-delivered with cytokine genes, using the same or different promoters and optionally with an internal ribosome binding site. Similiarly, α-1,3-galactosyl transferase expression on tumor cells allows complement-mediated cell killing.

As well, acquired or complex multispecific diseases, such as renal failure-induced erythropoietin deficiency, Parkinson's disease (dopamine deficiency), adrenal insufficiency, immune deficiencies, cyclic neutropenia, could be treated using a therapeutic gene delivered by a ligand. In some cases, vascular growth is desirable. As smooth muscle cells underlie the vasculature, delivery of endothelial growth factors, such as FGFs, especially FGF-2, VEGF, tie1, and tie2, through smooth muscle cells is advantageous.

2. Genes Encoding Protein Cytocides (Including Prodrugs - Negative Gene Therapy)

A cytocide-encoding agent is a nucleic acid molecule (e.g., DNA or RNA) that, upon internalization by a cell, and subsequent transcription (if DNA) and[/or] translation into a product is cytotoxic or cytostatic to a cell, for example, by inhibiting cell growth through interference with protein synthesis or through disruption of the cell cycle. Such a product may act by cleaving rRNA or ribonucleoprotein, inhibiting an elongation factor, cleaving mRNA, or other mechanism that reduces protein synthesis to a level such that the cell cannot survive. The product may be a protein, ribozyme, deoxyribozyme, antisense, and the like.

Examples of suitable products include, without limitation, saporin, the ricins, abrin, other ribosome inactivating proteins (RIPs), *Pseudomonas exotoxin*, inhibitors of DNA, RNA or protein synthesis, antisense nucleic acids, other metabolic inhibitors (e.g., DNA cleaving molecules), prodrugs (e.g., thymidine kinase from HSV and bacterial cytosine deaminase), light-activated porphyrin, ricin, ricin A chain, maize RIP, gelonin, diphtheria toxin, diphtheria toxin A chain, trichosanthin, tritin, pokeweed antiviral protein (PAP), mirabilis antiviral protein (MAP), Dianthins 32 and 30, abrin, monordin, bryodin, shiga, a catalytic inhibitor of protein biosynthesis from cucumber seeds (see, e.g., WO 93/24620), *Pseudomonas exotoxin*, biologically active fragments of cytotoxins and others known to those of skill in this art.

DNA molecules that encode an enzyme that results in cell death or renders a cell susceptible to cell death upon the addition of another product are preferred. Ribosome-inactivating proteins (RIPs), which include ricin, abrin, and saporin, are plant proteins that catalytically inactivate eukaryotic ribosomes. Ribosome-inactivating proteins inactivate ribosomes by interfering with the protein elongation step of protein synthesis. For example, the ribosome-inactivating protein saporin is an enzyme that cleaves rRNA and inhibits protein synthesis. Other enzymes that inhibit protein synthesis are especially well suited for use in the present invention. Any of these proteins, if not derived from mammalian sources, may use mammalian-preferred codons. Preferred codon usage is exemplified in *Current Protocols in Molecular Biology*, infra, and Zhang et al. (*Gene* 105:61, 1991).

A nucleic acid molecule encoding a prodrug may alternatively be used within the context of the present invention. Prodrugs are inactive in the host cell until either a substrate or an activating molecule is provided. As used herein, a "prodrug" is a compound that metabolizes or otherwise converts an inactive, nontoxic compound to a biologically, pharmaceutically, therapeutically, of toxic active form of the compound or is modified upon administration to yield an active compound through metabolic or other processes. Most typically, a prodrug activates a compound with little or no cytotoxicity into a toxic compound. Two of the more often used prodrug molecules, both of which are suitable for use in the present invention, are HSV thymidine kinase and *E. coli* cytosine deaminase.

Briefly, a wide variety of gene products which either directly or indirectly activate a compound with little or no cytotoxicity into a toxic product may be utilized within the context of the present invention. Representative examples of such gene products include HSVTK (herpes simplex virus thymidine kinase) and VZVTK (varicella zoster virus thymidine kinase), which selectively phosphorylate certain purine arabinosides and substituted pyrimidine compounds. Phosphorylation converts these compounds to metabolites that are cytotoxic or cytostatic. For example, exposure of the drugs ganciclovir, acyclovir, or any of their analogues (e.g., FIAU, FIAC, DHPG) to cells expressing HSVTK allows conversion of the drug into its corresponding active nucleotide triphosphate form.

Other gene products that may be utilized within the context of the present invention include *E. coli* guanine phosphoribosyl transferase, which converts thioxanthine into toxic thioxanthine monophosphate (Besnard et al., *Mol. Cell. Biol.* 7:4139–4141, 1987); alkaline phosphatase, which converts inactive phosphorylated compounds such as mitomycin phosphate and doxorubicin-phosphate to toxic dephosphorylated compounds; fungal (e.g., *Fusarium oxysporum*) or bacterial cytosine deaminase, which converts 5-fluorocytosine to the toxic compound 5-fluorouracil (Mullen, *PNAS* 89:33, 1992); carboxypeptidase G2, which cleaves glutamic acid from para-N-bis (2-chloroethyl) aminobenzoyl glutamic acid, thereby creating a toxic benzoic acid mustard; and Penicillin-V amidase, which converts phenoxyacetabide derivatives of doxorubicin and melphalan to toxic compounds (see generally, Vrudhula et al., *J. of Med. Chem.* 36(7):919–923, 1993; Kern et al., *Canc. Immun. Immunother.* 31(4):202–206, 1990). Moreover, a wide variety of Herpesviridae thymidine kinases, including both primate and non-primate herpesviruses, are suitable. Such herpesviruses include Herpes Simplex Virus Type 1 (McKnight et al., *Nuc. Acids Res* 8:5949–5964, 1980), Herpes Simplex Virus Type 2 (Swain and Galloway, *J. Virol.* 46:1045–1050, 1983), Varicella Zoster Virus (Davison and Scott, *J. Gen. Virol.* 67:1759–1816, 1986), marmoset herpesvirus (Otsuka and Kit, *Virology* 135:316–330, 1984), feline herpesvirus type 1 (Nunberg et al., *J. Virol.* 63:3240–3249, 1989), pseudorabies virus (Kit and Kit, U.S. Pat. No. 4,514,497, 1985), equine herpesvirus type I (Robertson and Whalley, *Nuc. Acids Res.* 16:11303–11317, 1988), bovine herpesvirus type I (Mittal and Field, *J. Virol* 70:2901–2918, 1989), turkey herpesvirus (Martin et al., *J. Virol.* 63:2847–2852, 1989), Marek's disease virus (Scott et al., *J. Gen. Virol.* 70:3055–3065, 1989), herpesvirus saimiri (Honess et al., *J. Gen. Virol.* 70:3003–3013, 1989) and Epstein-Barr virus (Baer et al., *Nature* (London) 310:207–311, 1984). Such herpesviruses may be readily obtained from commercial sources such as the American Type Culture Collection ("ATCC"; Manassas, Va.).

Furthermore, as indicated above, a wide variety of inactive precursors may be converted into active inhibitors. For example, thymidine kinase can phosphorylate nucleosides (e.g., dT) and nucleoside analogues such as ganciclovir (9-{[2-hydroxy-1-(hydroxymethyl)ethoxyl methyl} guanosine), famciclovir, buciclovir, penciclovir, valciclovir, acyclovir (9-[2-hydroxy ethoxy)methyl] guanosine), trifluorothymidine, 1-[2-deoxy, 2-fluoro, beta-D-arabino furanosyl]-5-iodouracil, ara-A (adenosine arabinoside, vivarabine), 1-beta-D-arabinofuranoxyl thymine, 5-ethyl-2'-deoxyuridine, 5-iodo-5'-amino-2,5'-dideoxyuridine, idoxuridine (5-iodo-2'-deoxyuridine), AZT (3' azido-3' thymidine), ddC (dideoxycytidine), AIU (5-iodo-5' amino 2', 5'-dideoxyuridine) and AraC (cytidine arabinoside). Other gene products may render a cell susceptible to toxic agents. Such products include tumor necrosis factor, viral proteins, and channel proteins that transport drugs.

Moreover, a cytocide-encoding agent may be constructed as a prodrug, which when expressed in the proper cell type is processed or modified to an active form. For example, the saporin gene may be constructed with an N- or C-terminal extension containing a protease-sensitive site. The extension renders the initially translated protein inactive and subsequent cleavage in a cell expressing the appropriate protease restores enzymatic activity.

The DNA sequences of these products are well known (see GenBank). nucleic acid molecule encoding one of the may be isolated by standard methods, such as amplification (e.g., PCR), probe hybridization of genomic or cDNA libraries, antibody screenings of expression libraries, chemically synthesized or obtained from commercial or other sources.

Additional types of cytocides that may be delivered according to the methods of the present invention are antibody molecules that are preferably expressed within the target cell; hence, these antibody molecules have been given the name "intrabodies." Conventional methods of antibody preparation and sequencing are useful in the preparation of intrabodies and the nucleic acid sequences encoding same; it is the site of action of intrabodies that confers particular novelty on such molecules. (For a review of various methods and compositions useful in the modulation of protein function in cells via the use of intrabodies, see published International Application No. WO 96/07321).

Intrabodies are antibodies and antibody derivatives (including single-chain antibodies or "SCA") introduced into cells as transgenes that bind to and incapacitate an intracellular protein in the cell that expresses the antibodies. As used herein, intrabodies encompass monoclonals, single chain antibodies, V regions, and the like, as long they bind to the target protein. Intrabodies to proteins involved in cell replication, tumorigenesis, and the like (e.g., HER2/neu, VEGF, VEGF receptor, FGF receptor, FGF) are especially useful.

For example, antibodies to HER2/neu (also called erbB-2) may be used to inhibit the function of this protein. HER2/neu has a pivotal role in the progression of certain tumors, human breast, ovarian and non-small lung carcinoma. Thus, inhibiting the function of HER2/neu may result in slowing or halting tumor growth (see, e.g. U.S. Pat. No. 5,587,458).

3. Antisense and Ribozymes

The nucleic acid condensate conjugates provided herein may also be used to deliver a ribozyme, antisense, and the like to targeted cells. Such products include antisense RNA, antisense DNA, ribozymes, deoxyribozymes, triplex-forming oligonucleotides, and oligonucleotides that bind proteins. The nucleic acids can also include RNA trafficking signals, such as viral packaging sequences (see e.g., Sullenger et al. *Science* 262:1566, 1994).

Nucleic acids and oligonucleotides for use as described herein can be synthesized by any method known to those of skill in this art (see, e.g., WO 93/01286, U.S. application Ser. No. 07/723,454; U.S. Pat. Nos. 5,218,088; 5,175,269; 5,109, 124). Identification of oligonucleotides and ribozymes for use as antisense agents and DNA encoding genes for delivery of gene therapeutics involve methods well known in the art. For example, the desirable properties, lengths and other characteristics of such oligonucleotides are well known. Antisense oligonucleotides may be designed to resist degradation by endogenous nucleolytic enzymes using linkages such as phosphorothioate, methylphosphonate, sulfone, sulfate, ketyl, phosphorodithioate, phosphoramidate, phosphate esters, and the like (see, e.g., Stein in: *Oligodeoxynucleotides. Antisense Inhibitors of Gene Expression*, Cohen, Ed, Macmillan Press, London, pp. 97–117, 1989); Jager et al., *Biochemistry* 27:7237, 1988).

Antisense nucleotides are oligonucleotides that bind in a sequence-specific manner to nucleic acids, such as mRNA or DNA. When bound to mRNA that has complementary sequences, antisense prevents translation of the mRNA (see, e.g., U.S. Pat. Nos. 5,168,053; 5,190,931; 5,135,917; 5,087, 617). Triplex molecules refer to single DNA strands that bind duplex DNA forming a colinear triplex molecule, thereby preventing transcription (see, e.g., U.S. Pat. No. 5,176,996).

Particularly useful antisense nucleotides and triplex molecules are molecules that are complementary or bind to the sense strand of DNA or mRNA that encodes a protein involved in cell proliferation, such as an oncogene or growth factor, (e.g., bFGF, int-2, hst-1/K-FGF, FGF-5, hst-2/FGF-6, FGF-8). Other useful antisense oligonucleotides include those that are specific for IL-8 (see, e.g., U.S. Pat. No. 5,241,049), c-src, c-fos H-ras (lung cancer), K-ras (breast cancer), urokinase (melanoma), BCL2 (T-cell lymphoma), IGF-1 (glioblastoma), IGF-1 receptor (glioblastoma), TGF-β1, and CRIPTO EGF receptor (colon cancer). These particular antisense plasmids reduce tumorigenicity in athymic and syngeneic mice.

A ribozyme is an RNA molecule that specifically cleaves RNA substrates, such as mRNA, resulting in inhibition or interference with cell growth or expression. There are at least five known classes of ribozymes involved in the cleavage and/or ligation of RNA chains. Ribozymes can be targeted to any RNA transcript and can catalytically cleave that transcript (see, e.g., U.S. Pat. No. 5,272,262; U.S. Pat. No. 5,144,019; and U.S. Pat. Nos. 5,168,053, 5,180,818, 5,116,742 and 5,093,246).

In addition, inhibitors of inducible nitric oxide synthase (NOS) and endothelial nitic oxide synthase are cytocides that are useful for delivery to cells. Nitric oxide (NO) is implicated to be involved in the regulation of vascular growth and tone in arterosclerosis. NO is formed from L-arginine by nitric oxide synthase (NOS) and modulates immune, inflammatory and cardiovascular responses.

The present invention also includes expression vectors including a nucleic acid segment encoding an enzymatic DNA or RNA molecule, preferably in a manner which allows expression of that nucleic acid molecule within a target cell. Thus, in general, an expression vector useful in conjunction with ribozymes or deoxyribozymes includes a bacterial, viral or eukaryotic promoter within a plasmid, cosmid, phagemid, virus, viroid, or phage vector. Other suitable vectors include double-stranded DNA (dsDNA), partially double-stranded DNA, dsRNA, partially dsRNA, or single-stranded RNA (ssRNA) or DNA (ssDNA). It should also be appreciated that useful vectors according to the present invention need not be circular.

It is also preferred that an enzymatic nucleic acid molecule-encoding nucleotide sequence is transcriptionally linked to a promoter sequence. For example, a vector according to the present invention may comprise an enzymatic RNA molecule under the control of a viral promoter, such as an Epstein-Barr Virus (EBV) promoter. A variety of viral promoters useful for this purpose are known in the art; see, e.g., those described in published PCT Application No. WO 93/23569, the disclosures of which are incorporated by reference herein.

Additional types of nucleic acids that may be condensed and stabilized according to the methods of the present invention are nucleic acids encoding antibody molecules that are preferably expressed within the target cell; hence, these antibody molecules have been given the name "intrabodies." For a review of various methods and compositions useful in the modulation of protein function in cells via the use of intrabodies, see published International Application No. WO 96/07321 and U.S. Pat. No. 5,587,458, to name but two examples.

C. EXCIPIENTS

In a therapeutic or laboratory context, it is generally not practical to administer the aforementioned condensates immediately after they are prepared. Therefore, condensates should be capable of withstanding storage in the liquid state for a practical amount of time, or they should be capable of being frozen and thawed—or lyophilized and reconstituted prior to use, all the while maintaining stability. One disadvantage of many previously-described formulations of DNA condensates is that subjecting the formulations to freezing results in an undesirable increase in particle size and a decrease in transgenic efficiency.

While not wishing to be bound by a particular theory, one possible explanation for this is that DNA complex particles are amorphous and do not form crystals at subambient temperatures. As the temperature drops, they remain in the liquid phase with other amorphous components, while the water which is present in the aqueous medium crystallizes out in the form of ice. As the water transforms into ice, the concentration of the DNA complex particles increases to a point at which the particles begin to aggregate and precipitate. In particular, if small ionic species are also present, even if their initial concentration is below the threshold at which they cause aggregation, as their concentration increases during freezing, ion-induced aggregation also occurs (described by Manning (1987) as "counterion condensation"). In view of the fact that pharmaceutical products often require the inclusion of small ionic species in the form of pH buffers and tonicity modifiers to be physiologically tolerated, formulating a product that can withstand freezing and also be ready-to-use after thawing or reconstitution if lyophilized, requires an additional stabilizer as in the present invention.

In addition, the formulations and condensates of the present invention are superior to other formulations described in the art for reasons unrelated to their superior storage and reconstitution stabilities. In particular, the compositions of the present invention are formulated such that once they are reconstituted, the amount of DNA (particle concentration) is greater than it was prior to reconstitution.

1. Zwitterions

Zwitterions are molecules that posses both positive and negative charges. According to the present invention, one way in which DNA:polycation condensates are made resistant to counterion condensation, as well as instability during prolonged liquid storage which may be caused by fluctuations in temperature or mechanical agitation, is to include a zwitterion in the formulation. Thus, if the formulation is to be frozen or lyophilized, it is desirable to add a zwitterion before subjecting it to freezing.

According to the Manning theory of counterion condensation, a zwitterion is unlikely to compete with either the polycation or the polyanion (i.e., the DNA), since the net charge of a zwitterion at physiological pH is usually zero. For many pharmaceutical applications, a zwitterion can substitute or be used in conjunction with dissociable ions for the purpose of maintaining physiological pH and isotonicity. Thus, zwitterions are particularly useful as stabilizers of nucleic acid:polycation complexes. Additionally, many zwitterions, such as the amino acids (e.g., glycine, histidine), are also strong chelators of metal ions, which provides the added advantage of improving stability of proteins and DNA which may be present in the formulations from metal catalyzed degradation.

Zwitterions which are useful in the present invention include, without limitation: zwitterionic buffers or "Biological buffers" such as HEPES, MES, TRIZMA, PIPES, MOPS, tricine, and taurine (see, e.g., The Sigma Catalog, "Biological Buffers", Sigma-Aldrich Co., Milwaukee, Wis., 1997); amino acids such as glycine and histidine; polypeptides that consist of various combinations of these and other amino acids; and short peptides such as glycylglycine and glutamyl lysine.

The amount of zwitterion to be added to the formulations of the present invention can be varied, but most often depends on the characteristics and amounts of the other components of the formulations, such as the nucleic acid and the polycation. In general, the zwitterion concentration is between about 5 mM and about 500 mM. In another embodiment the concentration is between about 10 mM and about 200 mM. In yet another embodiment the zwitterion concentration range is between about 20 mM and about 100 mM. The zwitterion preferably has a pKa of between about 3 to about 9, and more preferably between about 5 to about 8.

2. Amorphous Cryoprotectants and Crystalline Bulking Agents

In general, bulking agents which are commonly added to biomolecule-containing preparations to be lyophilized are crystalline in nature. Such crystal-forming substances alone are not well suited as bulking agents of DNA condensate preparations because crystal-formation during freezing/lyophilization can cause microenvironmental pH drift and concentration increases which can result in aggregation. The DNA:polycation condensates described herein must maintain their integrity during preparation and storage to ensure that the product is still efficacious when administered. For this reason, amorphous (i.e., non-crystal-forming) cryoprotectants are added to reduce the pH and concentration stress due to freezing of the formulations of the present invention.

Molecules which have the characteristics of amorphous cryoprotectants which are generally suitable for use in biological preparations other than nucleic acid condensation are well known. (See Tamiya, et al., *Cryobiology* 22:446, 1985, and Carpenter, J. K., and Crowe, L. M., *Cryobiology* 25:244, 1988.

Several screening methods may readily be used to determine which of these agents may also exhibit cryoprotectant properties for nucleic acid condensates; such methods are known in the art. To serve as a suitable cryoprotectant for use herein, the selected compound should be capable of reasonably lessening aggregation and/or loss of efficacy of the DNA:polycation during freezing/lyophilization and/or liquid storage of the formulation after thawing/reconstitution.

Amorphous cryoprotectants which are suitable for use herein include, mono, di, or oligosaccharides, polyols, and proteins, inter alia, albumin; disaccharides such as sucrose and lactose; monosaccharides such as fructose, galactose and glucose; poly alcohols such as glycerol and sorbitol; and hydrophilic polymers such as polyethylene glycol.

The amorphous cryoprotectant is preferably added to the formulations of the present invention before freezing, in which case it can also serves as a bulking agent. However, as a hydrophilic component, it may also provide for enhanced liquid stability. Thus, it may be desirable to add a cryoprotectant to formulations that are not intended to be frozen. In addition, as described above for the zwitterions, the addition of an amorphous cryoprotectant to DNA:polycation complexes for use in other applications besides therapeutics is also within the scope of the present invention.

With regard to crystalline bulking agents such agents are often used in the preparation of pharmaceutical compositions to provide the necessary bulk upon lyophilization. As discussed above, many types of crystalline bulking agents are known in the art. (See, Martini et al., PDA *J. Pharm Sci Tech* 51(2):62–67, 1997). Exemplary crystalline bulking agents include D-mannitol, trehalose, and dextran. As the aforementioned are exemplary only, one skilled in the art would recognize that any compound which, when included in the formulations of the present invention during freezing or lyophilization under given conditions, forms crystals, would be considered a suitable crystalline bulking agent. Within the context of the present invention a crystalline bulking agent is generally defined as a compound which can exist in a crystalline form and whose glass transition point (Tg) is below the temperature at which it is being freeze-dried. For example, a conventional freeze-dryer operates at a shelf-temperature from between about −10° C. to about −50° C. Therefore, in one embodiment, a crystalline bulking agent has a Tg below about −50° C.

D. LIGANDS

In one embodiment of the present invention the various compositions further comprise ligands. Numerous types of molecules are known to bind specific receptors on cells and they are suitable for use as a part of the condensation complexes produced by the herein-disclosed apparatuses and methods. Such molecules include those that are often identified in the art as "targeting ligands" or "ligands."Ligands suitable for use in the methods and compositions described herein include any peptide or polypeptide that has the ability to bind the target cell and be internalized. Any protein, polypeptide, analogue, or fragment that binds to a cell-surface receptor and is internalized may be used. These ligands may be produced by recombinant or other means in preparation for conjugation to the nucleic acid binding domain. The DNA sequences and methods to obtain the sequences of these receptor-binding internalized ligands are well known (U.S. Ser. No. 09/141,631). For example, useful ligands include those recited in published PCT Application Number WO 96/36362 and U.S. Ser. No. 08/718,404, the disclosures of which are incorporated by reference herein. Ligands may be optionally attached to the condensing agent to improve cell targeting or transfection efficacy.

As noted above, the present invention provides a variety of condensates, complexes, formulations, and compositions (collectively, "compositions"), including those which include ligands such as proteins (e.g., FGF proteins), polypeptides, analogs or mimics to assist in targeting the molecules and compositions of the present invention.

While certain ligands are described as exemplary, it will be appreciated by those of skill in the art that a wide variety of molecules may appropriately be used as ligands according to the within-disclosed compositions and methodologies. The following lists—while not exhaustive—will provide one with a better understanding of the variety of ligands available for use to specifically target preselected cells and to direct the composition, conjugate or complex with which the ligand is associated into the cell—and ideally, into the nucleus of said cell.

Useful ligand molecules include, without limitation, proteins that bind cancer cells, endothelial cells, cardiovascular cells, cells in the eye and the like. For example, ligands and ligand/receptor pairs include urokinase/urokinase receptor (GenBank Accession Nos. X02760/X74309); α-1,3 fucosyl transferase, α1-antitrypsin/E-selectin (GenBank Accession Nos. M98825, D38257/M87862); P-selectin glycoprotein ligand, P-selectin ligand/P-selectin (GenBank Accession Nos. U25955, U02297/L23088), VCAM1/VLA-4 (GenBank Accession Nos. X53051/X16983); E9 antigen (Blann et al., *Atherosclerosis* 120:221, 1996)/TGFβ receptor; Fibronectin (GenBank Accession No. X02761); type I α1- collagen (GenBank Accession No. Z74615), type I β2-collagen (GenBank Accession No. Z74616), hyaluronic acid/CD44 (GenBank Accession No. M59040); CD40 ligand (GenBank Accession No. L07414)/CD40 (GenBank Accession No. M83312); ELF-3, LERTK-2 ligands (GenBank Accession Nos. L37361, U09304) for elk-1 (GenBank Accession No. M25269); VE-cadherin (GenBank Accession No. X79981); ligand for catenins; ICAM-3 (GenBank Accession No. X69819) ligand for LFA-1, and von Willebrand Factor (GenBank Accession No. X04385), fibrinogen and fibronectin (GenBank Accession No. X92461) ligands for $\alpha_v\beta_3$ integrin (GenBank Accession Nos. U07375, L28832).

Other ligands include CSF-1 (GenBank Accession Nos. M11038, M37435); GM-CSF (GenBank Accession No. X03021); IFN-$\alpha$ (interferon) (GenBank Accession No. A02076; WO 8502862-A); IFN-$\gamma$ (GenBank Accession No. A02137; WO 8502624-A); IL-1-$\alpha$ (interleukin 1 alpha) (GenBank Accession No. X02531, M15329); IL-1-$\alpha$ (interleukin 1 beta) (GenBank Accession No. X02532, M15330, M15840); IL-1 (GenBank Accession No. K02770, M54933, M38756); IL-2 (GenBank Accession No. A14844, A21785, X00695, X00200, X00201, X00202); IL-3 (GenBank Accession No. M14743, M20137); IL-4 (GenBank Accession No. M13982); IL-5 (GenBank Accession No. X04688, J03478); IL-6 (GenBank Accession No. Y00081, X04602, M54894, M38669, M14584); IL-7 (GenBank Accession No. J04156); IL-8 (GenBank Accession No. Z11686); IL-10 (GenBank Accession No. X78437, M57627); IL-11 (GenBank Accession No. M57765 M37006); IL-13 (GenBank Accession No. X69079, U10307); TNF-$\alpha$ (Tumor necrosis factor) (GenBank Accession No. A21522); TNF-$\beta$ (GenBank Accession No. D12614); and GP30 ligand (S68256) for erbB2.

Still other ligands include PDGF (GenBank Accession No. X03795, X02811), angiotensin (GenBank Accession No. K02215), and all RGD-containing peptides and proteins, such as ICAM-1 (GenBank Accession No. X06990) that binds to integrin receptors. Other ligands include TNF$\alpha$ (GenBank Accession No. A21522, X01394), IFN-$\gamma$ (GenBank Accession No. A11033, A11034), IGF-I (GenBank Accession No. A29117, X56773, S61841, X56774, S61860), IGF-II (GenBank Accession No. A00738, X06159, Y00693), atrial naturietic peptide (GenBank Accession No. X54669), endothelin-1 (GenBank Accession No. Y00749), coagulation factor Xa (GenBank Accession No. L00395, L00396, L29433, N00045, M14327), TGF-$\beta$1 (GenBank Accession No. A23751), IL-1$\alpha$ (GenBank Accession No. X03833), and endoglin (GenBank Accession No. X72012).

Again, the foregoing lists are intended to be exemplary only and not exhaustive. As is also noted above, it is not essential that a ligand be included in all formulations and compositions of the present invention; rather, compositions and formulations that include ligands represent some of the many useful embodiments disclosed herein.

As noted above, any ligand that binds to a cell surface receptor and is internalized may be used within the context of this invention. Such ligands may comprise polypeptides or peptide analogues, including peptidomimetics. Ligands also include fragments of proteins, polypeptides, peptide analogues and peptide mimetics, or constrained analogues of such peptides that bind to the receptor and internalize a linked targeted agent. Polypeptides reactive with FGFR, e.g. members of the FGF family, including FGF-1 to FGF-15, are preferred. Modified peptides, especially those lacking proliferative function, and chimeric peptides, which retain the specific binding and internalizing activities, are also contemplated for use herein. Especially preferred are polypeptides reactive with the FGF high affinity receptor.

Modification of the polypeptide may be effected by any means known to those of skill in this art. One preferred method relies on modification of DNA encoding the polypeptide and expression of the modified DNA. DNA encoding a receptor-binding (and preferably internalizing) ligand may be mutagenized using standard methodologies. For example, cysteine residues that are responsible for aggregate formation may be deleted or replaced. If necessary, the identity of cysteine residues that contribute to aggregate formation may be determined empirically, by deleting and/or replacing a cysteine residue and ascertaining whether the resulting protein aggregates in solutions containing physiologically acceptable buffers and salts. In addition, fragments of these receptor-binding internalized ligands may be constructed and used. The binding region of many of these ligands have been delineated.

Mutations may be made by any method known to those of skill in the art, including site-specific or site-directed mutagenesis of DNA encoding the protein and the use of DNA amplification methods using primers to introduce and amplify alterations in the DNA template, such as PCR splicing by overlap extension (SOE). Site-directed mutagenesis is typically effected using a phage vector that has single- and double-stranded forms, such as M13 phage vectors, which are well-known and commercially available. Other suitable vectors that contain a single-stranded phage origin of replication may be used (see, e.g., Veira et al., *Meth. Enzymol.* 15:3, 1987).

Suitable conservative substitutions of amino acids are well-known and may be made generally without altering the biological activity of the resulting molecule. For example, such substitutions are generally made by interchanging within the groups of polar residues, charged residues, hydrophobic residues, small residues, and the like. If necessary, such substitutions may be determined empirically merely by testing the resulting modified protein for the ability to bind to and internalize upon binding to the appropriate receptors. Those that retain this ability are suitable for use in the formulations, compositions, and methods herein. As such, an amino acid residue of a receptor-binding internalized ligand is non-essential if the polypeptide that has been modified by deletion or alteration of the residue possesses substantially the same ability to bind to its receptor and internalize a linked agent as the unmodified polypeptide.

If the formulation is to include a such ligands, conjugates of the ligand to a polycation may be carried out essentially as follows. Typically, a receptor-binding ligand is coupled to a polycation by chemical conjugation, usually via linkers, as described previously. The selected linker or linkers is (are) linked to the receptor-binding internalized ligands by chemical reaction, generally relying on an available thiol or amine group on the receptor-binding internalized ligands. Heterobifunctional linkers are particularly well suited for chemical conjugation. Alternatively, if the linker is a peptide linker, then the linker may be connected to the ligand as a fusion protein.

In such compositions, the ligand is usually conjugated to the polycation prior to condensation to form a polycation-ligand conjugate. When using such a nucleic acid:polycation-ligand conjugate ratio is usually less than about 1:5 (w/w). Although it is possible to form stable polycation-ligand conjugates via ionic interactions, in preferred compositions, the ligand is covalently attached to the polycation. Exemplary ligands include for example, FGF, an FGF mutein, a fragment of an FGF, or a fragment of an FGF mutein.

Measuring proliferative activity provides a convenient way of monitoring receptor binding and uptake of ligands that retain such activity after modification. For example, all of the FGF proteins induce mitogenic activity in a wide variety of normal diploid mesoderm-derived and neural crest-derived cells and this activity is mediated by binding to an FGF cell surface receptor followed by internalization. A test of such "FGF mitogenic activity", which reflects the ability to bind to FGF receptors and to be internalized, is the ability to stimulate proliferation of cultured bovine aortic endothelial cells (see, e.g., Gospodarowicz et al., *J. Biol. Chem.* 257:12266–12278, 1982; Gospodarowicz et al., *Proc. Natl. Acad. Sci. USA* 73:4120–4124, 1976).

If the FGF or other growth factor ligand has been modified so as to lack mitogenic activity, binding and internalization may still be readily assayed by any one of the following tests or other equivalent tests. Generally, these tests involve labeling the ligand, incubating it with target cells, and visualizing or measuring intracellular label. Alternatively, the ligand can be conjugated with a polycation by any of the methods described herein and complexed with a plasmid encoding a therapeutic sequence. As discussed herein, the complex may be used to transfect cells and its activity measured.

CONDENSATE PREPARATION

A. CONDENSATION OF THE NUCLEIC ACID WITH POLYCATION OR LIGAND-POLYCATION CONJUGATE

The ratio of DNA to polycation will naturally depend on the characteristics of the components, such as the number and distribution of positively charged groupings on the polycation, and the length of the nucleic acid. Thus, the ratio may vary widely among different constructs. An appropriate ratio can be determined by starting with a ratio that approximates charge neutrality and evaluating lower and higher ratios, until a ratio can be determined which provides for optimal internalization and therapeutic effect. Accordingly, for each pair of nucleic acid and polycation condensing agent, there exists a unique nucleic acid:polycation ratio (by weight) at which the resultant nucleic acid condensate preparations possess three distinct characteristics: (1) the average particle size reaches a maximum, (2) zeta potential of nucleic acid condensate particles approaches a minimum net charge, and (3) an absence of either free (or unbound) nucleic acid or polycation in the preparation. This ratio has been designated as the "Critical Condensation Ratio" or "CCR".

It is believed that the CCR coincides with the ratio of components such that charge neutrality is achieved-that is, the negative charges on the nucleic acid are completely neutralized by the positive charges on the polycation molecules within a nucleic acid molecule condensate particle. The CCR can be readily determined using laser-light scattering, zeta potential measurement and composition analysis for free nucleic acid and/or polycation. The CCR value is, therefore, a very important parameter for determining the nucleic acid:polycation mixing ratio. For example, in order to achieve complete condensation of the nucleic acid, the nucleic acid:polycation mixing ratio should not exceed the CCR otherwise free, uncomplexed nucleic acid will exist in the preparation and as such this nucleic acid will not be compacted. When nucleic acid and polycation are mixed at the CCR, nucleic acid molecule condensate particles generated are usually unstable and highly aggregated possibly due to the lack of net surface charge or a repulsive force between particles. Such aggregated nucleic acid molecule condensates are also considered to be undesirable. When the nucleic acid molecule:polycation mixing ratio is below the CCR, free polycation molecules are present and the nucleic acid molecule condensate particles generated are usually small (ca. 100–200 nm) and stable with a net positive surface charge (positive zeta potential). In one embodiment, stable nucleic acid molecule condensates are prepared by adjusting the ratio of nucleic acid molecule:polycation such that about 5% to about 80% (by weight) of the total polycation is free. In yet another embodiment the ratio of nucleic acid molecule:polycation is adjusted such that about 5% to about 50% (by weight) of the total polycation is free. In a further embodiment the ratio of nucleic acid molecule:polycation is adjusted such that about 5% to about 15% (by weight) of the total polycation is free.

For stabilization, excipients are included in the reaction mixture containing polycation or the ligand-polycation conjugate and the nucleic acids during the condensation reaction. For preparing complexes, the nucleic acid is diluted and added to the polycation or conjugate, along with various excipients, and gently agitated. Mixing is continued until condensation is essentially complete. A condensation reaction is usually complete within minutes or less and is easily verified by laser-light scattering where the average particle size (ZAve) remains unchanged over a period of a few hours. Aggregation (or a higher order condensation) is usually detected when the ZAve increases continuously within the first 2–5 hours of the condensation reaction.

In addition to complexation via electrostatic binding of the nucleic acid to the polycation, the complex needs to be "condensed" for efficient uptake by a cell, but not to the point at which the complex aggregates and falls out of solution. The point at which the formulation has been condensed, but not aggregated, can be determined by laser-light scattering. Conditions such as pH, salt concentration, nucleic acid:polycation ratio and concentration and excipient concentration can be easily optimized to avoid aggregation. It has been reported that small ionic species such as sodium chloride and sodium phosphate at higher concentrations compete with the larger charged constituents of the formulation, i.e., the positively charged polycation (Manning, 1987). Accordingly, the concentration of reduced small ionic species should be below the level at which aggregation is observed. The concentration of the small cationic molecule depends on the size and concentration of the polycation. In most of the examples presented the FGFK84 concentration was 100 ug/ml and, therefore, the concentration of small cationic molecules should be lower than 30 mM so as to avoid particle aggregation. The length of DNA is irrelevant to condensate formation, provided that sufficient polycation is provided to neutralize the majority of DNA phosphate groups.

In Table 1 below, several exemplary condensate formulations are given. These formulations were prepared with 50 $\mu$g/ml plasmid DNA and 100 $\mu$g/ml FGF-polylysine in a total volume of 500 $\mu$l.

TABLE 1

Exemplary Condensate Formulations

| Sample # | pH | Additives | Total Concentration | Average Particle Size, n = 3 (nm) |
|---|---|---|---|---|
| 1 | 7.0 | Glycine | 100 mM | 84 ± 3 |
| 2 | 7.0 | Histidine | 100 mM | 128 ± 4 |
| 3 | 4.0 | Glu + Arg | 25 mM | 87 ± 3 |
| 4 | 5.0 | Glu + Arg | 25 mM | 106 ± 3 |

TABLE 1-continued

Exemplary Condensate Formulations

| Sample # | pH | Additives | Total Concentration | Average Particle Size, n = 3 (nm) |
|---|---|---|---|---|
| 5 | 6.0 | Glu + Arg | 25 mM | 89 ± 2 |
| 6 | 7.0 | Glu + Arg | 25 mM | 78 ± 3 |
| 7 | 8.0 | Glu + Arg | 25 mM | 77 ± 2 |
| 8 | 9.0 | Glu + Arg | 25 mM | 80 ± 4 |
| 9 | 7.0 | Hepes | 100 mM | 97 ± 4 |
| 10 | 7.0 | Gly-Gly | 100 mM | 90 ± 3 |
| 11 | 7.0 | D-mannitol | 5% (w/v) | 121 ± 3 |
| 12 | 7.0 | Glycerol | 5% (w/v) | 102 ± 2 |
| 13 | 7.0 | Sucrose | 5% (w/v) | 100 ± 2 |
| 14 | 7.0 | Trehalose | 5% (w/v) | 103 ± 4 |
| 15 | 7.0 | Tween 80 | 0.05% (w/v) | 65 ± 2 |
| 16 | 7.0 | Glycine Sucrose | 20 mM 5% (w/v) | 88 ± 3 |

*All amino acids are L isomeric form.

1. Efficacy Testing

The complexes are tested in vitro and in vivo for the desired biological effect. Thus, if the nucleic acid encodes a cytocide, cell cytotoxicity or inhibition of protein synthesis or other function is measured. Cell death is conveniently assayed by counting the number of living cells in the presence and absence of delivery. Other assays, such as MTS, $^3$H-leu uptake, $^3$H-thymidine incorporation, flow cytometry, or staining cells with vital dyes are also suitable. For in vivo use pharmaceutical products often require the inclusion of small ionic species in the form of pH buffers and tonicity modifiers to be physiologically tolerated. Formulating a product that can withstand freezing and also be ready-to-use after thawing or reconstitution if lyophilized, requires an additional stabilizer.

The amount of compaction and shape of compaction may be measured in several different ways. Visualization by electron microscopy (EM), atomic force microscopy (AFM), and laser-light scattering (LLS) can be used to determine the average size of DNA condensates. In one embodiment laser light scattering, also known as photon correlation spectroscopy (PCS) or dynamic light scattering (DLS) is used. Such scattering methods analyze the time dependence of intensity fluctuations in scattered laser light due to the Brownian motion of particles in a solution/suspension. Since small particles diffuse more rapidly than large particles, the rate of fluctuation of scattered light intensity varies accordingly. Thus, using an autocorrelation analysis of time dependence of intensity fluctuations in scattered light, the translational diffusion coefficient (D) of the particles can be measured, which in turn can be used to determine the mean hydrodynamic diameter of the particles using the Stokes-Einstein equation.

To test ligand containing compositions, receptor binding and internalization may be measured by the following two assays. (1) A competitive inhibition assay of the condensates to cells expressing the appropriate receptor demonstrates receptor binding. (2) Receptor binding and internalization may be assayed by measuring expression of a reporter gene, such as β-galactosidase (β-gal) or luciferase (Luc) (e.g., enzymatic activity), in cells that have been transfected with a condensate of a plasmid encoding a reporter gene and a conjugate of a receptor-binding ligand and nucleic acid binding domain. This assay is particularly useful for optimizing conditions to give maximal transfection. Thus, the optimum ratio of receptor-binding internalized ligand/nucleic acid binding domain to nucleic acid and the amount of DNA transgene expression may readily be determined by assaying and comparing the enzymatic activity of β-gal. As such, these first two assays are useful for preliminary analysis and failure to show receptor binding or β-gal activity does not per se eliminate a candidate receptor-binding internalized ligand/nucleic acid binding domain conjugate or fusion protein from further analysis.

2. Other Preparations

As demonstrated throughout the detailed description and in the following examples, a variety of compositions are provided. Such compositions may take the form of a particles in a liquid medium, frozen medium, or as a lyophile. In one aspect of the invention, the nucleic acid containing particles may be lyophilized to form a lyophile or lyophilized powder, which can be reconstituted using a reconstituting medium prior to use. In such compositions, preferred particle sizes after reconstitution have a hydrodynamic diameter of less than about 200 nm. Further, by utilizing the excipients described herein to enhance stability, it is possible to reconstitute the lyophile to a final nucleic acid concentration that is greater than the concentration before lyophilization. As such, DNA concentrations prior to lyophilization can be less than about 0.5 mg/ml while reconstituted concentrations can remain stable at concentrations of less than about 20 mg/ml. Such concentrated formulations are particularly useful for therapeutic applications that require high particle concentrations to achieve sufficient cellular uptake. In other embodiments the average particle size after reconstitution is less than twice the particle size before lyophilization.

In addition, as demonstrated throughout, in various embodiments the particles of the present invention remain stable upon freezing as well as multiple freeze-thaw cycles, and over a variety of storage conditions. For example, in some embodiments the particles remain stable for at least 7 days at temperatures between about 2 to about 8° C., while in other embodiments the particles remain stable for one month or more.

PHARMACEUTICAL APPLICATIONS

The condensates provided herein are useful in the treatment and prevention of various diseases, syndromes, and hyperproliferative disorders. As used herein, "treatment" means any manner in which the symptoms of a condition, disorder or disease are ameliorated or otherwise beneficially altered. Treatment also encompasses any pharmaceutical use of the compositions herein. As used herein, "amelioration" of the symptoms of a particular disorder refers to any lessening, whether permanent or temporary, lasting or transient, that can be attributed to or associated with administration of the composition.

A. PREPARATION OF PHARMACEUTICAL COMPOSITIONS

Pharmaceutical carriers or vehicles suitable for administration of the complexes provided herein include any such carriers known to those skilled in the art to be suitable for the particular mode of administration. In addition, the complexes may be formulated as the sole pharmaceutically active ingredient in the composition or may be combined with other active ingredients.

The complexes can be administered by any appropriate route, for example, orally, parenterally, including intravenously, intradermally, subcutaneously, or topically, in liquid, semi-liquid or solid form and are formulated in a manner suitable for each route of administration. Preferred modes of administration depend upon the indication treated. Dermatological and ophthalmologic indications will typically be treated locally; whereas, tumors and restenosis, will typically be treated by systemic, intradermal, or intramuscular modes of administration.

Preferably, the compositions are substantially pure. As used herein, "substantially pure" means sufficiently homogeneous to appear free of readily detectable impurities as determined by standard methods of analysis, such as thin layer chromatography (TLC), gel electrophoresis, high performance liquid chromatography (HPLC), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers. In such instances, further purification might increase the specific activity of the compound.

Therapeutically effective concentrations and amounts may be determined for each application herein empirically by testing the complexes in known in vitro and in vivo systems (e.g., murine, rat, rabbit, or baboon models), such as those described herein; dosages for humans or other animals may then be extrapolated therefrom.

If administered intravenously, suitable carriers include physiological saline or phosphate buffered saline (PBS), and solutions containing thickening and solubilizing agents, such as glucose, polyethylene glycol, and polypropylene glycol and mixtures thereof. Liposomal suspensions may also be suitable as pharmaceutically acceptable carriers. These may be prepared according to methods known to those skilled in the art.

The compositions may be prepared with carriers that protect them against rapid elimination from the body, such as time release formulations or coatings. Such carriers include controlled release formulations, such as, but not limited to, implants and microencapsulated delivery systems, and biodegradable, biocompatible polymers, such as ethylene vinyl acetate, polyanhydrides, polyglycolic acid, polyorthoesters, polylactic acid and others. For example, the composition may be applied during surgery using a sponge, such as a commercially available surgical sponges (see, e.g., U.S. Pat. Nos. 3,956,044 and 4,045,238; available from Weck, Alcon, and Mentor), that has been soaked in the composition and that releases the composition upon contact with the area of interest.

B. INCORPORATION OF COMPLEXES INTO DELIVERY MATRICES

For certain applications, it may be useful to incorporate the complexes of the present invention into matrices which are designed for administration to specific tissue sites. In such applications, cell specificity may be achieved through selection and administration of the matrix itself, in which case it may not be necessary to incorporate a ligand which reacts with a cell surface. For examples of matrices which are adapted for wound healing and are thus useful in conjunction with the complexes of the present invention, see, e.g., U.S. Pat. No. 5,763,416 and Published International Application Nos. WO95/22611, WO97/38729, WO96/20698, and WO97/47254, to name but a few.

In one exemplary embodiment, the compositions of the present invention are incorporated into matrices which have been adapted for the purpose of tissue regeneration. In this application, the compositions may be loaded into matrices which provide a scaffold for recruitment of cells, in which case the complexes need not be cell specific. In such embodiments, it may be possible to condense the DNA directly into the matrix during matrix formation. In another embodiment, the matrix is preformed and impregnated with the nucleic acid compositions of the present invention.

OTHER BIOLOGICAL APPLICATIONS

In addition to the aforementioned therapeutic applications, the present invention is generally useful whenever the stability of nucleic acid condensates is desired. In a laboratory setting, the stability of nucleic acid condensates is important whenever procedures are being performed which compromise the structural integrity and functionality of the nucleic acid.

The following examples are included for illustrative purposes only and are not intended to limit the scope of the invention.

EXAMPLES

Example 1

FORMATION AND MAINTENANCE OF SMALL DNA CONDENSATES IN AQUEOUS SOLUTIONS

To generate test particles of DNA:polycation condensates for particle size and in vitro transgene expression analyses, we used a plasmid DNA coding for a reporter gene such as pSVβ for β-galactosidase or pLuc for luciferase and a polycation condensing agent FGFK84. FGFK84 is a disulfide-linked chemical conjugate of basic fibroblast growth factor (FGF2) and poly-D-lysine with an average chain length of 84 lysine residues. The mixing ratio of DNA:FGFK84 is fixed at 2:1 by weight. The condensation reaction was carried out by first mixing an appropriate amount of the DNA with a desired additive in a small tube, to which FGFK84 was added (approx. volume 500 $\mu$l). The solution was mixed immediately by gentle pipetting up and down 3–5 times. Unless stated otherwise, the final concentrations were fixed at 50 $\mu$g/mL for DNA and 100 $\mu$g/mL for FGFK84. The condensation mixture was then incubated at room temperature for 1 hour prior to particle size analysis by laser light scattering and transgene expression assay.

The average hydrodynamic diameter of DNA condensates was measured by a laser light scattering instrument (Zetasizer 5000, Malvern, Worcestershire, WR, UK). All experiments were performed with an argon-ion laser operating at 488 nm wavelength and a power output of 15 mW. The sample was placed in a cylindrical scattering cell surrounded by a water bath to maintain a constant temperature of 25° C. and particle size was measured at a fixed angle of 90°. The hydrodynamic diameter values (Zave) for all DNA condensate preparations were derived using Cumulants Analysis algorithm. For all laser light scattering measurements, the average hydrodynamic diameter is expressed as the average of 4–8 measurements with a standard deviation of less than 5%.

The in vitro transgene expression assay is based on a colorimetric measurement of a substrate subjected to enzymatic conversion by an enzyme encoded by the plasmid DNA of interest (β-galactosidase or luciferase). Unless stated otherwise, most assays were conducted using the β-galactosidase method. β-galactosidase (β-gal) gene expression assays were performed on baby hamster kidney (BHK) cells. Approximately 15,000 BHK cells were seeded in a 24-well plate 24 hours prior to addition of the DNA condensate. Various amounts of DNA from 1.5 $\mu$g to 2.5 $\mu$g were added to each well in triplicate followed by spinning at 2,500 rpm in a tabletop centrifuge(CS-6R, Beckman) for 45 minutes at 28° C. The plates were then incubated at 37° C. in the presence of 5% $CO_2$ for 72 hours prior to β-gal activity assay. Cells were washed once with phosphate-buffered saline (PBS) and then treated with 0.2% Triton X-100 lysis buffer for 10–15 minutes followed by 15 minute vigorous rotation. Cell lysates were transferred to 1.5 mL microfuge tubes and centrifuged for 3 minutes at 13,500 g at 4° C. to pellet cell debris. 10 $\mu$l of supernatant was used for β-gal or luciferase activity analysis using Clonetech's assay kit (Palo Alto, Calif.). Protein concentration was determined by BCA assay (Pierce, Rockford, Ill.) using bovine serum albumin (BSA) as a standard. The β-gal or luciferase activity was normalized to milligrams of protein and micrograms of DNA input. A freshly prepared DNA condensate generated in 5% D-mannitol was used as an assay control in order to correct for inherent day-to-day variation.

Various additives were evaluated for their effect on the maintenance of the stability of small DNA cparticles during the condensation reaction and storage in an aqueous solution. The additives selected included the common pharmaceutical and biological excipients such as sodium chloride, sodium phosphate, HEPES, D-mannitol, sucrose, trehalose, glycerol, L-glycine, L-histidine and L-glycylglycine. These additives were applied at the concentration levels that are considered to be physiologically acceptable. As shown in FIG. 1, DNA condensates formed in water or in the presence of 100 mM zwitterionic molecules such as L-glycine, histidine, glycyl-glycine and HEPES, pH 7, or 5% (w/v) sugar or polyols including D-mannitol, sucrose, trehalose, and glycerol, or the combination of 5% sucrose and 20 mM glycine were all small in size with average diameters of about 100 nm. In contrast, DNA condensates formed in PBS (phosphate buffered saline) or 150 mM NaCl were much larger and unstable with an average diameter of over 1000 nm observed 1 hour after condensation and the condensates eventually fell out of solution after a few hours.

Figure 2:
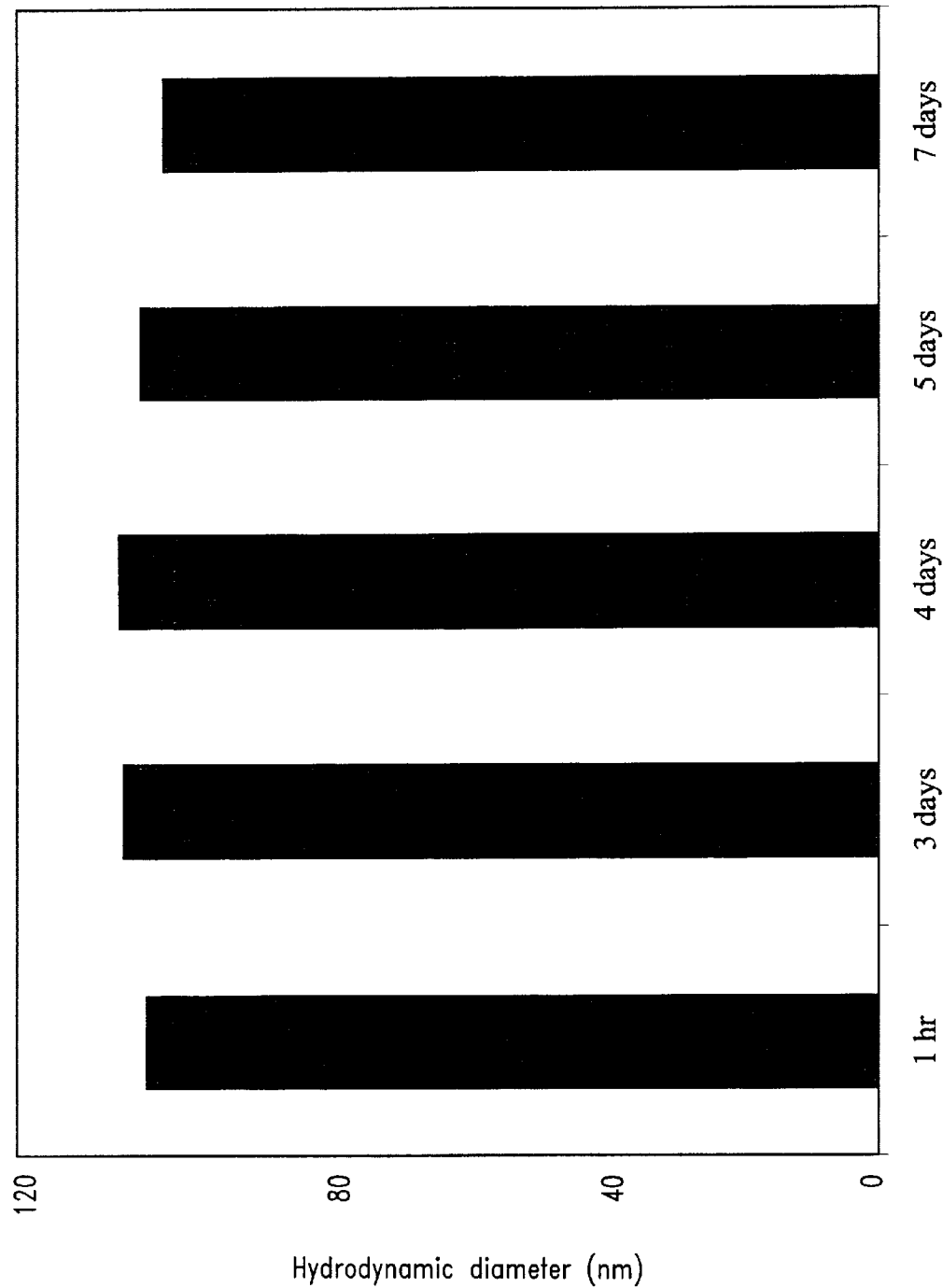
FIG. 2 is a graph depicting the effects of time on particle size for samples stored at 37° C.

To further evaluate the storage stability of DNA condensate particles in an aqueous state, DNA condensates generated at 100 $\mu$g/mL DNA and 200 $\mu$g/mL FGFK84 in the presence of 5% (w/v) D-mannitol were incubated at 37° C. for up to 7 days. As seen in FIG. 2, DNA condensate particle size remained stable at about 100 nm when incubated at 37° C. for at least 7 days.

In conclusion, it appears that both nonionic and zwitterionic additives are compatible with DNA condensates during the condensation reaction and storage in an aqueous solution. Nonionic saccharides and polyols such as sucrose, trehalose and D-mannitol are pharmaceutically useful excipients which are commonly used as freeze-drying bulking agent, cryoprotectant for the active drug substances, or as tonicity modifiers. Similarly, zwitterionic additives such as HEPES or glycine may serve as pH buffer and metal chelator to stablize metal sensitive components in the formulations. Dissociable ionic compounds such as sodium chloride and sodium phosphate, on the other hand, destablize DNA condensates, resulting in aggregates and subsequent precipitation of the particles.

Example 2

MAINTENANCE OF DNA CONDENSATE PARTICLE SIZE AND TRANSGENE EXPRESSION DURING FREEZE-THAW TREATMENT

Figure 3A:
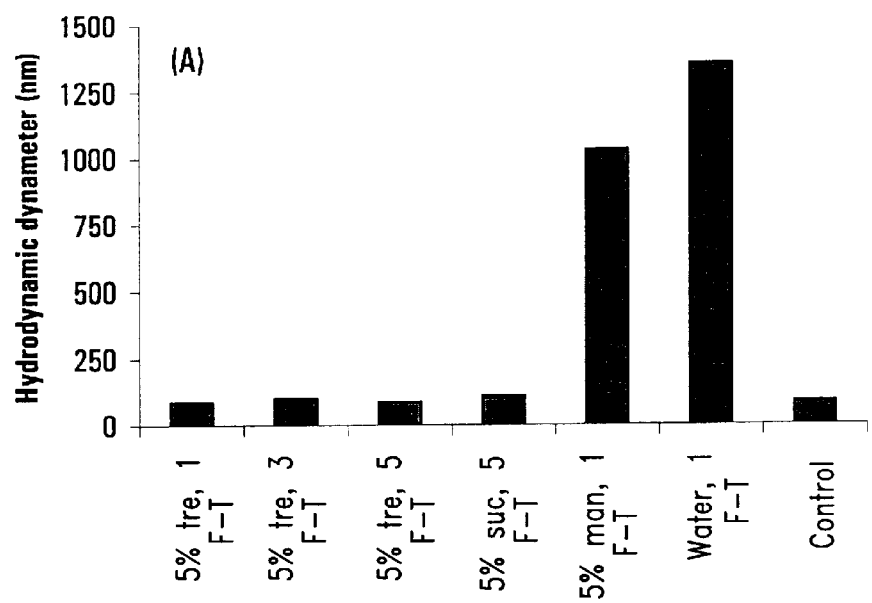
FIGS. 3A and 3B are graphs depicting the effects of freeze-thaw cycles on particle size (3A) and transgenic expression of DNA (3B) using various excipients as described in Example 2.

In order to evaluate the effect of various excipients on DNA condensates when subjected to freeze-thaw treatment, freshly prepared DNA condensates of 50 $\mu$g/mL DNA (PSVβ) and 100 $\mu$g/mL FGFK84 in the presence of 5% trehalose, 5% sucrose, 5% D-mannitol or no additive were incubated at room temperature for 1 hour and subjected to freezing at −20° C. for at least 2 hours followed by thawing at room temperature. This process was repeated for 1, 3 and 5 freeze-thaw cycles prior to particle size measurement and transgene expression assay. As shown in FIG. 3A, DNA condensate particle size was stably maintained by trehalose or sucrose at 90–110 nm after multiple freeze-thaw cycles, whereas the samples containing no additive or D-mannitol were very sensitive to freeze-thaw treatment with significant increase in size observed.

Figure 3B:
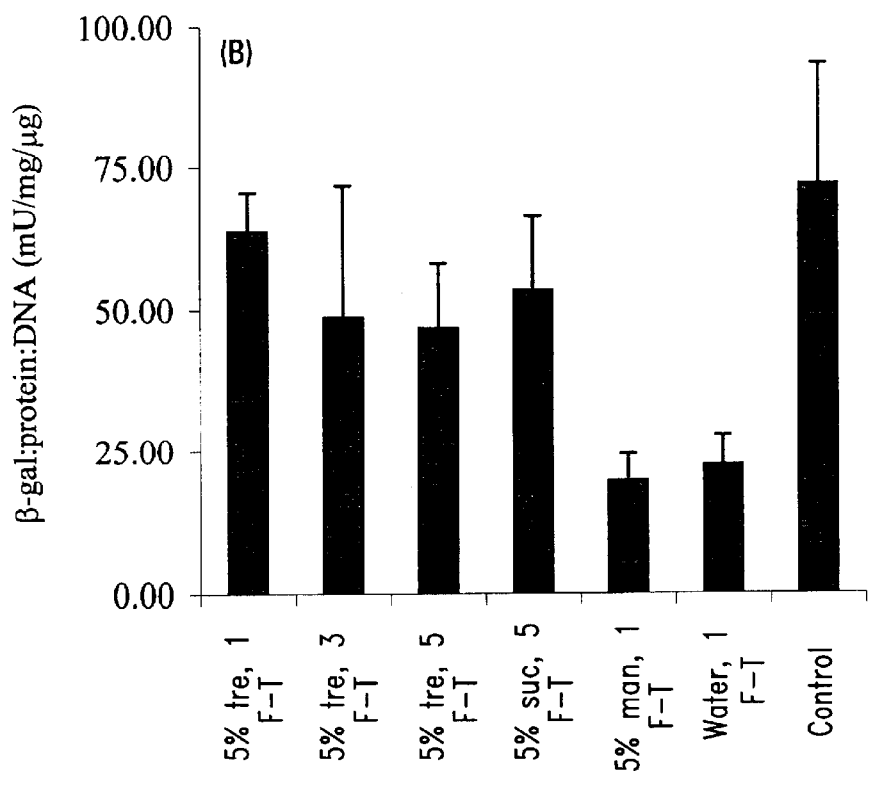

To examine the biological activity of freeze-thaw treated DNA condensates, transgene expression of these samples were tested and compared. As shown in FIG. 3B, β-gal activity of trehalose or sucrose protected DNA condensates was comparable (40–60 mU/mg/$\mu$g) within the experimental error to the pre-treatment controls. In contrast, the aggregated DNA condensates generated in water or 5% D-mannitol after a single freeze-thaw treatment lost about 50% of the original transgene activity.

In conclusion, it appears that amorphous additive species such as trehalose and sucrose are capable of protecting DNA condensates against freeze-thaw induced stress. In contrast, an absence of such amorphous additive or a presence of a crystalline additive such as D-mannitol failed to protect the DNA condensate from freeze-thaw induced aggregation and loss of transgene activity.

Example 3

MAINTENANCE OF DNA CONDENSATE STABILITY DURING LYOPHILIZATION

To prepare DNA condensate lyophiles, DNA condensation was carried out to obtain a final concentration of 50 $\mu$g/mL DNA (pSV-βgal) and 100 $\mu$g/mL FGFK84 in the presence of various additives. The condensation mixture was incubated at room temperature for 1 hour followed by a controlled freezing in a programmable freezing apparatus (Cryomed, Model 1010, Forma Scientific) at −1° C./min to −40° C. The frozen samples were placed under vacuum (ca. 50 mTorr) on a labconco freeze-dry system (LyohLock 4.5, Kansas City, Kans.) and maintained under vacuum for 48–72 hr. The lyophilized DNA condensates were reconstituted in water and analyzed by laser light scattering and β-gal activity assay.

Figure 4A:
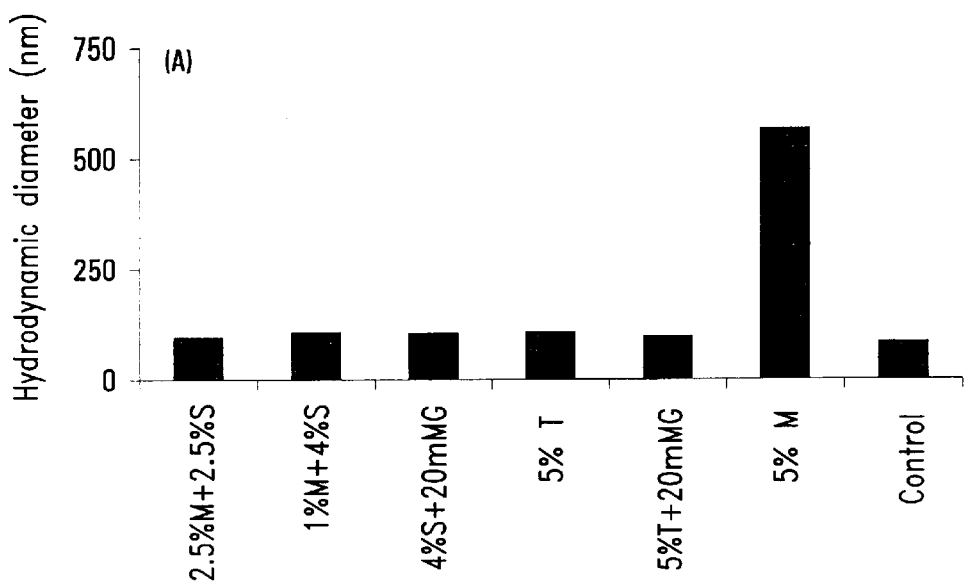
FIGS. 4A and 4B are graphs depicting the effects of lyophilization on particle size (4A) and gene expression (4B) using various excipients as described in Example 3.
Figure 4B:
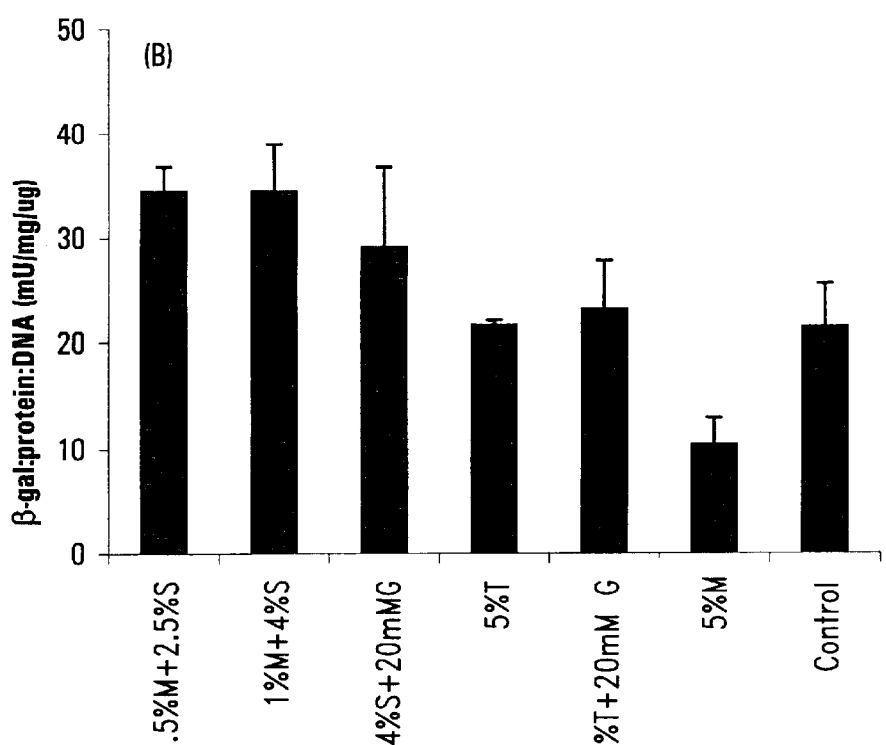

As shown in FIG. 4A, DNA particles formed in the presence of sucrose and trehalose or in combination with D-mannitol and zwitterionic molecules remained unchanged at about 100 nm, while those formed with D-mannitol only increased dramatically to 566 nm. Transgene expression results of the lyophilized DNA particles are presented in FIG. 4B. Samples containing sucrose or trehalose maintained transgene expression of 20–30 mU/mg/$\mu$g and compared favorably with the freshly prepared control. In contrast, transgene activity of lyophilized particles formed in D-mannitol alone decreased by about 50%.

In conclusion, these data indicate that an amorphous excipient such as sucrose or trehalose is required to maintain a stable particle size throughout the freeze-drying and reconstitution process, whereas DNA condensates with only a crystalline additive such as D-mannitol added are not capable of withstanding the stress during the freezing, freeze-drying or reconstitution step as evidenced by the increased particle size. While an amorphous excipient alone performed well in preserving the DNA condensate particle stability, they failed to facilitate the formation of a well-defined lyophile bulk. To obtain physically stable and aesthetically acceptable bulk lyophile, D-mannitol was mixed with the amorphous additive (e.g. sucrose) which resulted in lyophiles that are comparable to the D-mannitol lyophile bulk in appearance while maintaining small DNA condensate particles. In addition, zwitterionic molecules such as L-glycine can be mixed with the sucrose without any negative impact on the DNA condensate particle size. Such zwitterionic additives may serve as a pH buffer or metal chelator as needed in a lyophile formulation. In summary, this experiment revealed that, with an amorphous additive or more preferably a combination of an amorphous and a crystalline or an amorphous and a zwitterionic excipient, it is possible to lyophilize DNA condensates while maintaining their particle size and transgene activity intact.

Example 4

INCREASE IN DNA CONDENSATE CONCENTRATION BY LYOPHILIZATION

Figure 5:
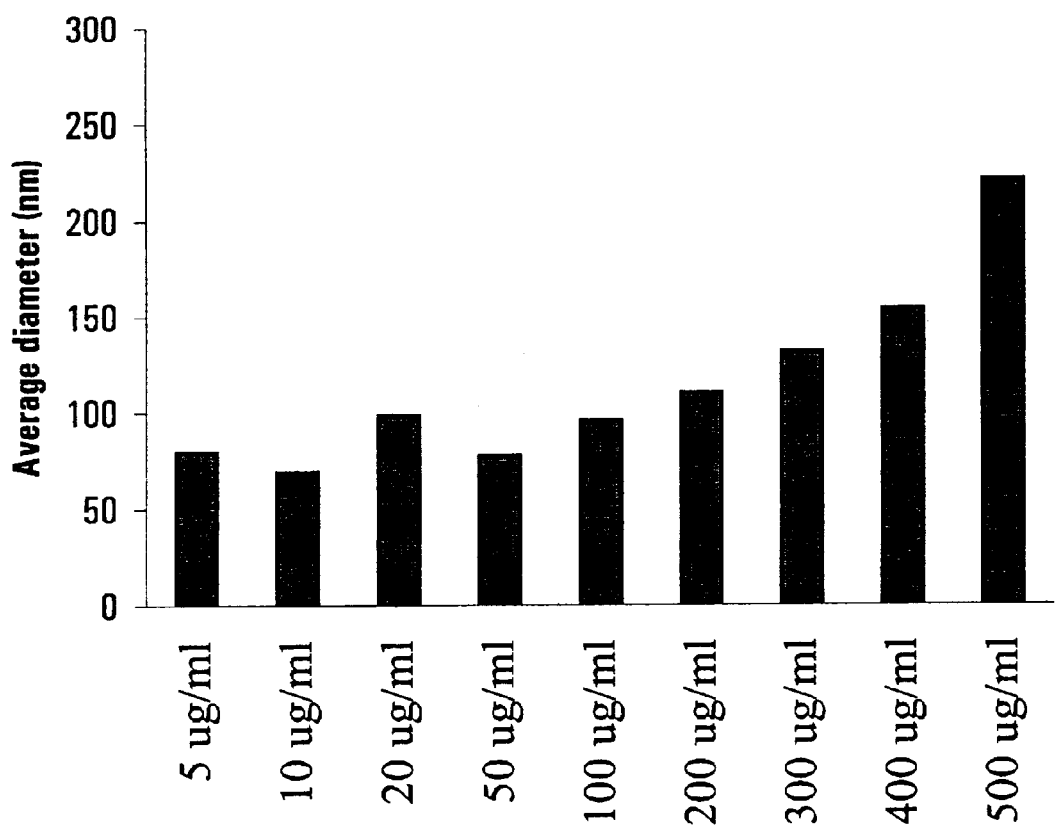
FIG. 5 is a graph depicting the effects of DNA concentration on particle size using sucrose as an excipient.

The objective of this study was to achieve very high DNA condensate concentrations which are often required for preclinical or clinical evaluation. A low concentration of DNA condensates would limit the dose of DNA condensates obtainable for in vivo evaluations when injection volume is also limited. DNA condensation at DNA concentration >250 $\mu$g/mL yields large particles (>200 nm). For example, the particle size of DNA condensates prepared in 5% (w/v) sucrose remained at about 100 nm for starting DNA concentrations up to 250 $\mu$g/mL, then gradually increases at DNA concentrations greater than 250 $\mu$g/mL as shown in FIG. 5. Therefore, high concentrations of DNA condensates are not achievable simply by performing the condensation reaction at a higher initial DNA concentration.

Figure 6A:
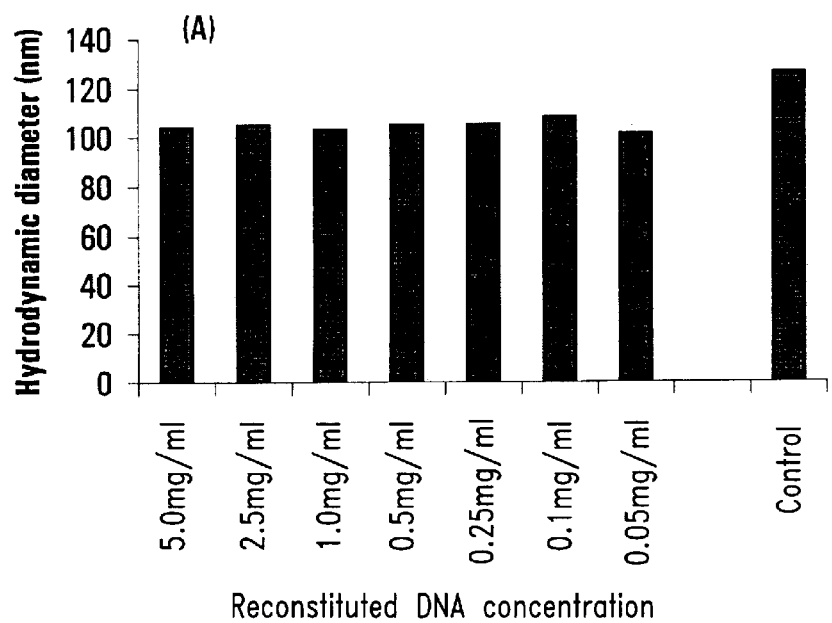
FIGS. 6A and 6B are graphs depicting the effects of increased DNA concentration by lypholization on particle size (6A) and gene expression (6B) as described in Example 4.
Figure 6B:
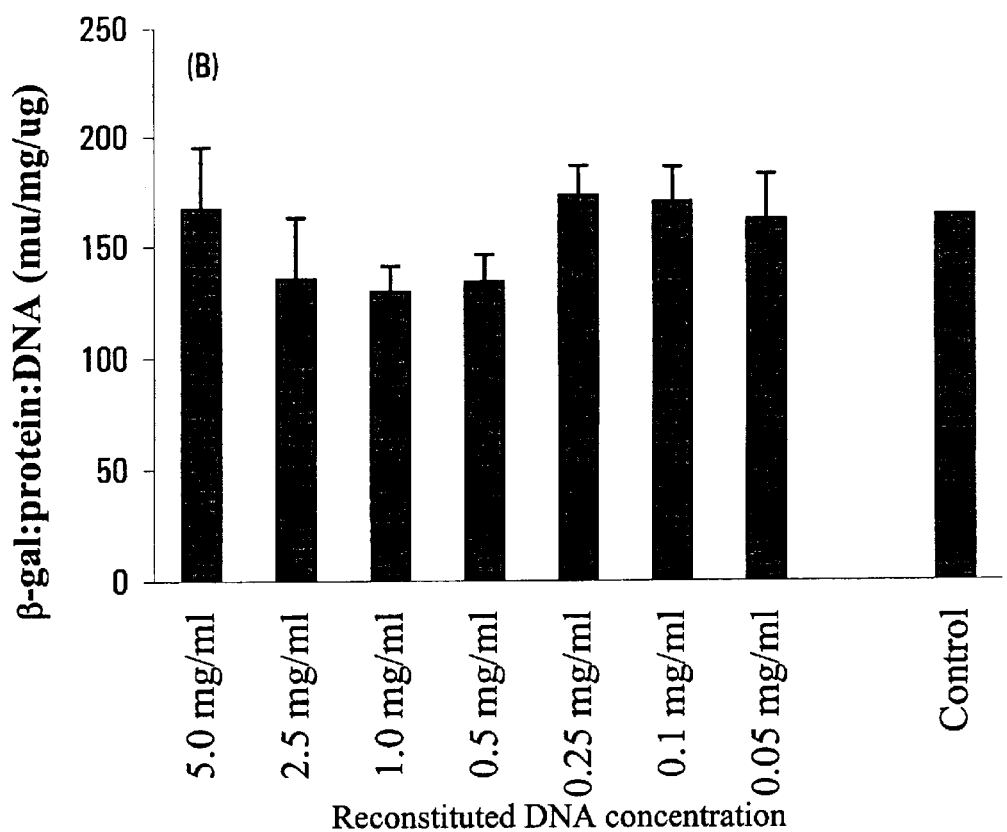

In this experiment, DNA condensates were prepared in a dilute form and lyophilized as described in Example 3. Then the lyophile was reconstituted in a fraction of the initial volume to obtain a series of increased concentrations. For example, the condensation reaction was performed to obtain a final 100 $\mu$g/mL DNA and 200 $\mu$g/mL FGFK84 in the presence of 0.5% sucrose and 0.25% D-mannitol. The lyophilized samples were reconstituted with various volumes of water to achieve DNA condensate concentrations from 50 $\mu$g/mL to 5 mg/mL. The reconstituted DNA condensates were incubated at 25° C. for 5 hours prior to particle size and transgene expression analyses. As shown in FIG. 6A, reconstituted DNA condensates even at 5 mg/mL concentration yielded small stable particles (ca. 100 nm) when stored at room temperature (22–25° C.) for at least 5 hours. In addition comparable transgene expression was observed at all concentrations tested from 50 $\mu$g/mL to 5 mg/mL (FIG. 6B).

In conclusion, formulations together with a process have been developed which permit very high DNA concentrations of at least 5 mg/ml of DNA condensates to be achieved.

Example 5

EFFECT OF ADDITIVE CONCENTRATION ON PARTICLE SIZE AND TRANSGENE EXPRESSION

Using the strategy illustrated in Example 4, DNA condensates can be prepared through lyophilization/reconstitution to concentrations up to at least 5 mg/mL DNA or a 50-fold or more increase in concentration with respect to the pre-lyophilization DNA concentration. However, the resulting fold increase in additive concentration may be unacceptablly high for use in in vivo studies. For example, a total concentration >10% (w/v) of sucrose or sucrose/D-mannitol combination would be considered hypertonic and generally undesirable. Studies were conducted in an effort to determine the minimum excipient concentration needed for maintaining stable DNA condensates throughout the entire lyophilization and reconstitution process.

Figure 7A:
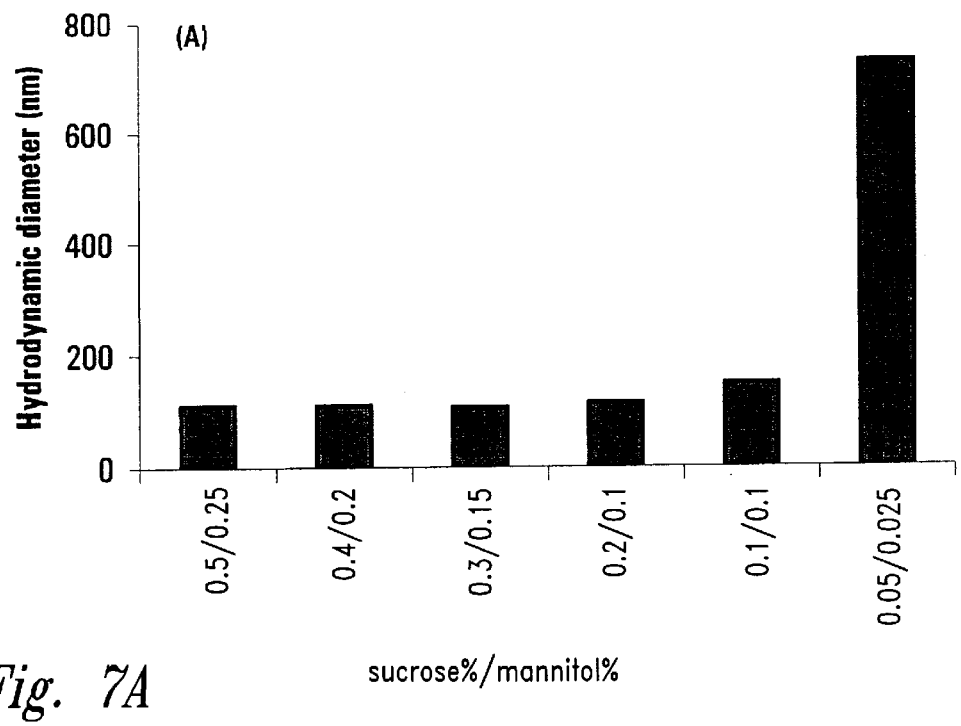
FIGS. 7A and 7B are graphs depicting the effect of sugar concentration on particle size (7A) and gene expression (7B), as described in Example 5.
Figure 7B:
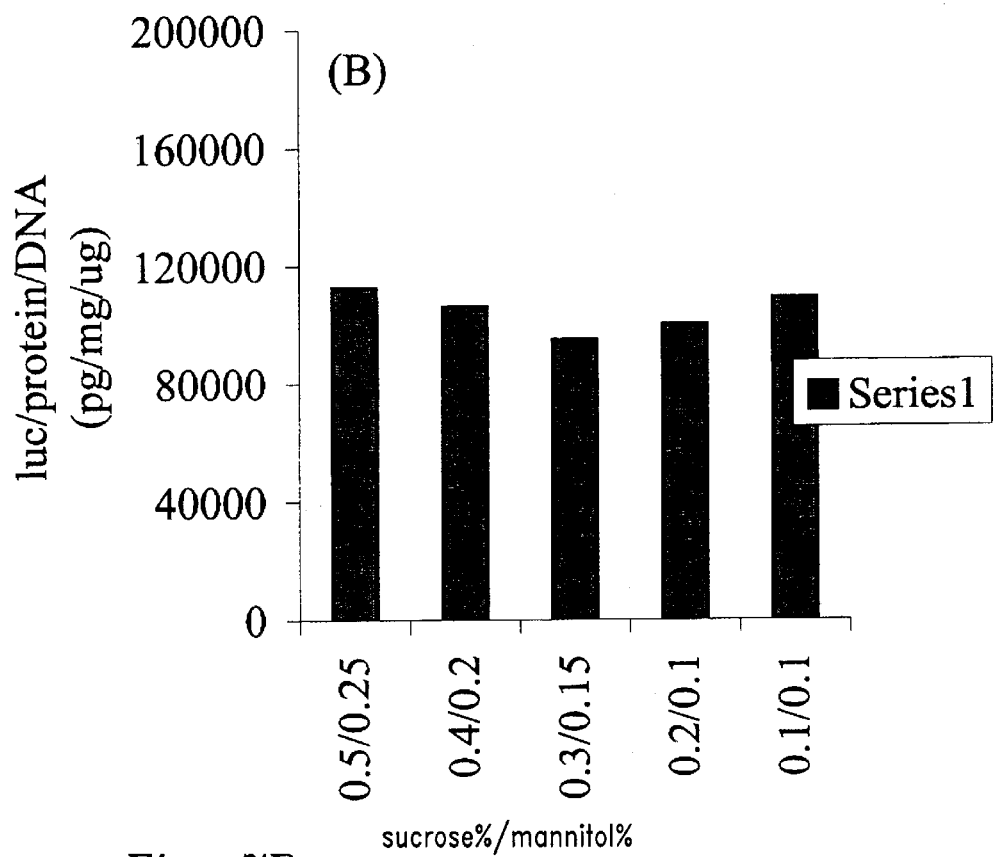

To study the effect of total excipient concentration on particle size and transgene expression, DNA condensation was performed in the presence of various amounts of a combination of sucrose and D-mannitol from a total of 0.75% to 0.075% (w/v) in order to determine the lower limit of sugar concentration required to maintain small particles of about 100 nm. FIG. 7A shows that DNA condensates remain at about 100 nm, after reconstitution, for additive concentration as low as 0.2% (0.1% sucrose and 0.1% D-mannitol). Particle size increased to 730 nm as the total additive concentration was decreased to 0.075% (0.05% sucrose and 0.025% D-mannitol). Samples which maintained stable particle size of about 100 nm were examined for transgene expression. As noted in FIG. 7B, plasmid containing luciferase reporter gene was used for this experiment and transgene expression was expressed as picograms of luciferase detected per milligram of total protein and per microgram of DNA input. Comparable transgene expression was observed for all samples processed with different amounts of sucrose/D-mannitol.

In conclusion, formulations which can effectively protect DNA condensates during lyophilization and reconstitution have been developed using a combination of amorphous and crystalline additives (sucrose and D-mannitol) at concentrations as low as 0.1% (w/v) for each component. This low excipient concentration facilitates the accomplishment of a stable DNA condensate preparation at very high concentration while achieving a more pharmaceutically desired formulation of excipients. Such formulations and concentration process are considered to be very useful in providing a wide dose range of DNA condensates for in vivo studies.

Example 6

REAL TIME AND ACCELERATED STABILITY OF LYOPHILIZED DNA CONDENSATES

Figure 8A:
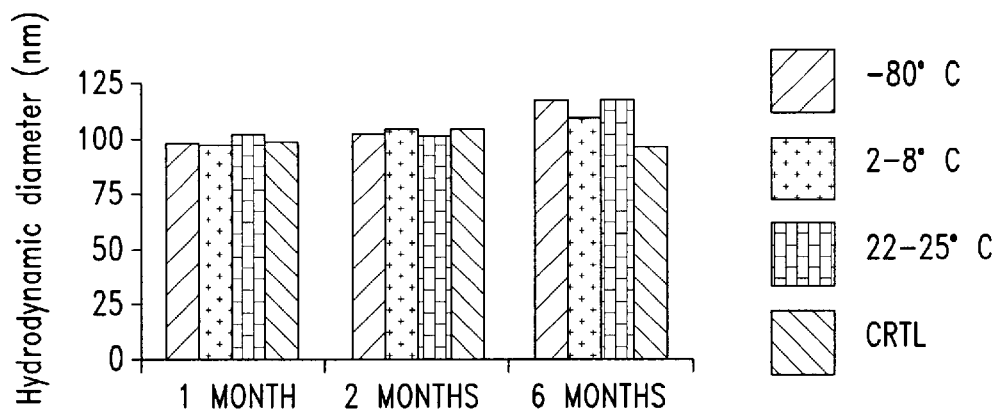
FIGS. 8A and 8B are graphs depicting the effects of long-term storage of DNA lyophiles on particle size (8A) and gene expression (8B) as described in Example 6.
Figure 8B:
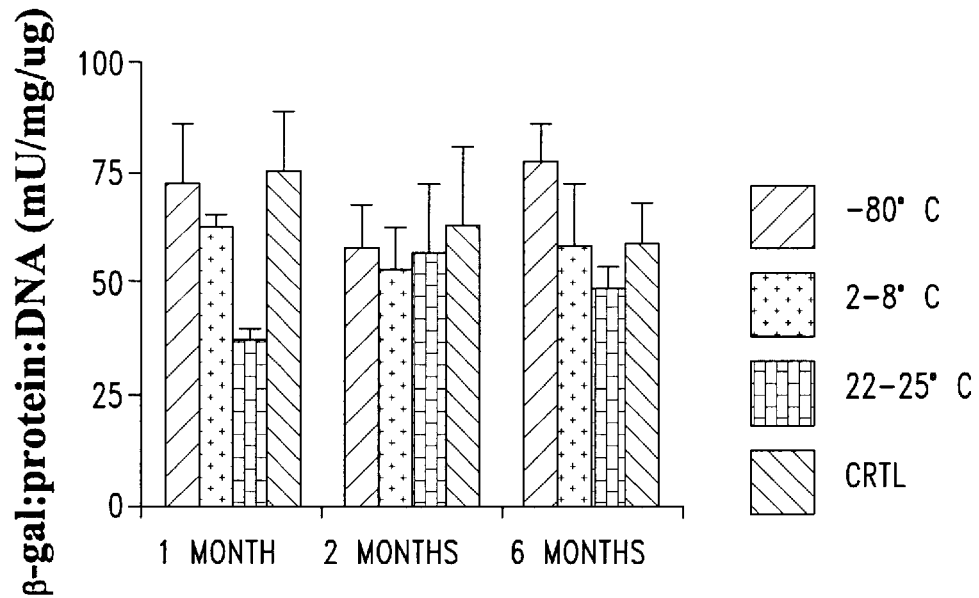

For a commercially viable therapeutic product, a long term shelf-life which maintains both physical and biological properties of the therapeutic is essential. To evaluate the long term stability of DNA condensate lyophiles, DNA condensation was carried out at 50 $\mu$g/mL pSV$\beta$ and 100 $\mu$g/mL FGFK84 in 2.5% sucrose, 2.5% D-mannitol and 20 mM L-glycine, pH 7.0. Sucrose was selected for maintaining small particle size during lyophilization while D-mannitol was added to ensure a morphologically acceptable lyophile bulk. Glycine was included in order to maintain physiological pH and a total additive concentration of ca. 5% was chosen to achieve a physiological isotonic formulation upon reconstitution. Lyophile samples were incubated at −80° C., 2–8° C. and room temperature (22–25° C.). At each time point, samples were reconstituted with Water for Injection, USP (WFI) to obtain a DNA condensate concentration of 50 $\mu$g/mL DNA. Hydrodynamic diameter measurement, transgene expression and residual moisture determination using a Karl Fischer titrator were performed. As shown in FIG. 8, DNA condensates incubated at −80° C., 2–8° C. and room temperature remained stable with respect to both particle size and transgene expression activity for at least six months. The hydrodynamic diameters remained at about 100 nm at all temperatures for the 6 month period and comparable transgene expression was observed to the control. The control was freshly prepared at 50 µg/mL DNA and 100 µg/mL FGFK84 in 5% D-mannitol as described in Example 1. Transgene expression of the 1 month room temperature sample appeared reduced by about 50%. However, this decrease in β-gal activity was not observed for either the 2 or 6 month room temperature samples, suggesting that the transgene activity of the DNA condensates stored at RT is largely preserved for at least 6 months. The residual moisture of lyophiles measured by Karl Fischer titrator was approximately 2–4% (wt. %).

Figure 9A:
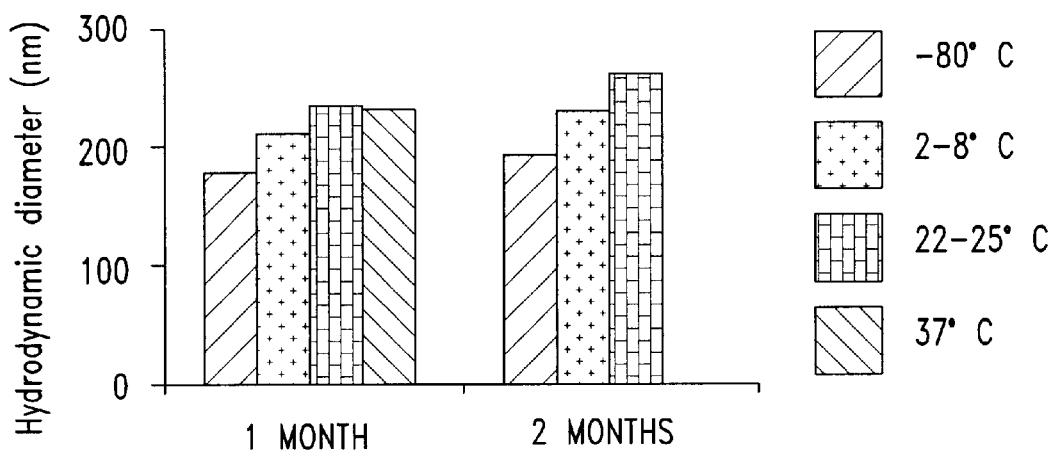
FIGS. 9A and 9B are graphs depicting the effects of long-term storage of lyophilized FGFK82:DNA condensates on particle size (9A) and gene expression (9B), as described in Example 6.
Figure 9B:
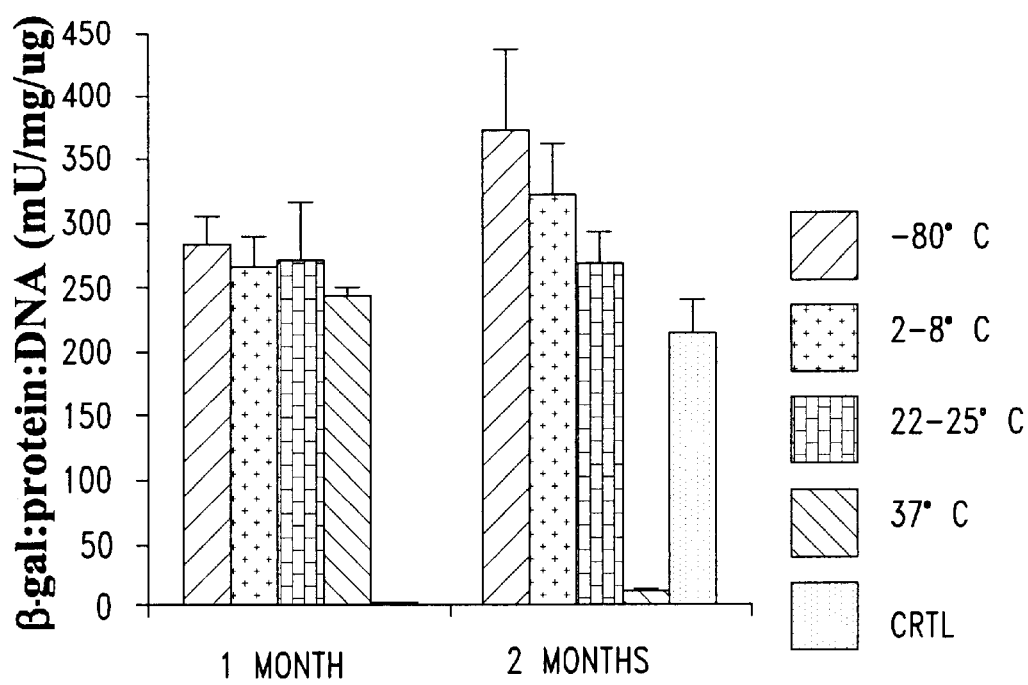

Another FGF-polylysine conjugate, FGFK82, was also used to condense DNA and the real-time and accelerated stability of the DNA condensates was monitored in a similar manner as described above. In this study, DNA condensation was performed at 50 µg/mL DNA and 150 µg/mL FGFK82 in 2.5% sucrose, 2.5% D-mannitol and 20 mM L-glycine, pH 7.0 followed by lyophilization. Lyophile samples were stored at −80° C., 2–8° C., room temperature (22–25° C.) and 37° C. for 1 and 2 months prior to reconstitution. Hydrodynamic diameter measurements and transgene expression assays were performed. FIG. 9 presents data showing that the hydrodynamic diameter remained stable and comparable transgene expression to the control was observed at all temperatures tested when stored for 1 month. For samples stored for 2 months, stable particle size and comparable transgene expression to the control was observed at −80° C., 2–8° C. and 22–25° C. However, for DNA condensates stored at 37° C. for 2 months no particles were detected and subsequently no transgene expression was detected.

In conclusion, DNA condensate lyophiles prepared with a combination of amorphous and crystalline additives (sucrose and D-mannitol, respectively) in a zwitterionic pH buffer (glycine), pH 7 appeared to be stable at room temperature (22–25° C.) for at least 6 months in terms of particle size and in vitro transgene activity. It is clear that the DNA condensate lyophiles possess a much better prognosis for long term stability and therefore are believed to be more commercially feasible than either liquid or frozen product formulations.

Numerous modifications may be made to the foregoing systems without departing from the basic teachings thereof. Although the present invention has been described in substantial detail with reference to one or more specific embodiments, those of skill in the art will recognize that changes may be made to the embodiments specifically disclosed in this application, yet these modifications and improvements are within the scope and spirit of the invention as set forth in the claims which follow. All publications, patents, and patent applications cited in this specification are incorporated herein by reference as if each such publication, patent, or patent application was specifically and individually indicated to be incorporated herein by reference.

We claim:

1. A composition comprising a nucleic acid condensed with a polycation in a liquid medium, thereby forming a particle, and at least one excipient selected from the group consisting of a zwitterion, an amorphous cryoprotectant, a crystalline bulking agent, and mixtures thereof wherein the particle increases in size by less than one-fold during storage in the liquid medium for one week at about 2° C. to about 8° C.

2. The composition according to claim 1, wherein the excipient comprises a zwitterion, an amorphous cryoprotectant, and a crystalline bulking agent.

3. The composition according to claim 1, wherein the excipient comprises an amorphous cryoprotectant and a crystalline bulking agent.

4. The composition according to claim 1, wherein the excipient comprises at least one zwitterion selected from the group consisting of an amino acid, a polypeptide, and a biological buffer.

5. The composition according to claim 1, wherein the zwitterion comprises glycine or polypeptide comprising at least one glycine residue.

6. The composition according to claim 4, wherein the amino acid has a pKa in the range of about 3 to about 9.

7. The composition according to claim 6, wherein the amino acid is histidine.

8. The composition according to claim 1, wherein the amorphous cryoprotectant is selected from the group consisting of a saccharide, a polyol and a protein.

9. The composition according to claim 8, wherein the amorphous cryoprotectant is a saccharide.

10. The composition according to claim 1, wherein the crystalline bulking agent is selected from the group consisting of D-mannitol, trehalose, and dextran.

11. The composition according to claim 1, wherein the polycation is selected from the group consisting of a polyamino acid, protamine, histone, and a polymer.

12. The composition according to claim 11, wherein the polyamino acid comprises one or more cationic and/or basic amino acids.

13. The composition according to claim 11, wherein the polyamino acid is selected from the group consisting of poly-L-lysine, poly-D-lysine and poly-DL-lysine.

14. The composition according to claim 1, wherein the nucleic acid is a genome or plasmid DNA comprising a therapeutic or diagnostic gene.

15. The composition according to claim 1, wherein the nucleic acid concentration is less than about 20 mg/ml.

16. The composition according to claim 1, wherein said polycation concentration is less than about 40 mg/ml.

17. The composition according to claim 1, wherein the nucleic acid:polycation charge ratio is less than 1:1.

18. The composition according to claim 1, wherein the nucleic acid:polycation charge ratio is between about 1:1 to about 1:2.

19. The composition according to claim 1, wherein the particle increases in size less than one-fold during storage in the liquid medium for one week at about 20° C. to about 28° C.

20. The composition according to claim 1, further comprising a ligand.

21. The composition according to claim 20, wherein the ligand is attached to the polycation thereby forming a polycation-ligand conjugate.

22. The composition of claim 20, wherein the ligand is a polypeptide reactive with a cell growth factor receptor.

23. A condensate, comprising a nucleic acid, a polycation, and at least one excipient selected from the group consisting of a zwitterion, an amorphous cryoprotectant, a crystalline bulking agent, and mixtures thereof.

24. The condensate according to claim 23, wherein the excipient comprises a zwitterion, an amorphous cryoprotectant, and a crystalline bulking agent.

25. The condensate according to claim 23, wherein the excipient comprises at least one zwitterion selected from the group consisting of an amino acid, a polypeptide, and a biological buffer.

26. The condensate according to claim 23, wherein the excipient comprises a cryoprotectant and a crystalline bulking agent.

27. The condensate according to claim 23, wherein the condensate comprises a mixture of a first zwitterion and a second zwitterion.

28. The condensate according to claim 23, wherein the amorphous cryoprotectant is selected from the group consisting of a saccharide, a polyol, and a protein.

29. The condensate according to claim 23, wherein the crystalline bulking agent is selected from the group consisting of D-mannitol, trehalose, and dextran.

30. The condensate according to claim 23, wherein the polycation is selected from the group consisting of a polyamino acid, protamine, histone, and a polymer.

31. The condensate according to claim 23, wherein the nucleic acid is a genome or plasmid DNA comprising a therapeutic or diagnostic gene.

32. The condensate according to claim 23, wherein the nucleic acid concentration is less than about 20 mg/ml.

33. The condensate according to claim 23, wherein the polycation concentration is less than about 40 mg/ml.

34. The condensate according to claim 23, wherein the nucleic acid:polycation charge ratio is less than 1:1.

35. The condensate according to claim 23, wherein the nucleic acid:polycation charge ratio is between about 1:1 to about 1:2.

36. The condensate according to claim 23, wherein, the condensate forms a particle and wherein the particle increases in size less than one-fold during storage in a liquid medium for one week at about 2° C. to about 8° C.

37. The composition according to claim 23, further comprising a ligand.

38. The composition according to claim 37, wherein the ligand is attached to the polycation.

39. A lyophile prepared by the process comprising the steps:
   (a) combining water, nucleic acid, polycation, and an excipient, thereby forming a plurality of particles; and
   (b) removing water from (a).

40. The lyophile according to claim 39, wherein the excipient is selected from the group consisting of a zwitterion, an amorphous cryoprotectant, a crystalline bulking agent, and mixtures thereof.

41. The lyophile according to claim 40, wherein substantially all of the water is removed.

42. The lyophile according to claim 39, wherein the excipient comprises a zwitterion, an amorphous cryoprotectant, and a crystalline bulking agent.

43. The lypophile according to claim 39, wherein the excipient comprises at least one zwitterion selected from the group consisting of an amino acid, a polypeptide, and a biological buffer.

44. The lyophile according to claim 39, wherein the excipient comprises an amorphous cryprotectant and a crystalline bulking agent.

45. The lyophile according to claim 40, wherein the lyophile comprises a mixture of a first zwitterion and a second zwitterion.

46. The lyophile according to claim 40, wherein the amorphous cryoprotectant is selected from the group consisting of a saccharide, a polyol, and a protein.

47. The lyophile according to claim 40, wherein the crystalline bulking agent is selected from the group consisting of D-mannitol, trehalose, and dextran.

48. The lyophile according to claim 39, wherein the polycation is selected from the group consisting of a polyamino acid, protamine, histone, and a polymer.

49. The lyophile according to claim 39, wherein the lypophile is reconstituted in a liquid medium to provide particles and wherein the particles increase in size by less than one-fold as compared to particles before lyophilization.

50. The lyophile according to claim 39, further comprising a ligand.

51. A composition comprising components:
   (a) a nucleic acid;
   (b) a polycation;
   (c) an excipient; and
   further comprising a ligand covalently attached to at least one of the components and wherein the composition comprises a particle that increases in size by less than one-fold during storage in a liquid medium for one week at about 2° C. to about 8° C.

52. The composition according to claim 51, wherein the ligand is covalently conjugated to the polycation forming a polycation-ligand conjugate.

53. The composition according to claim 52, wherein the ratio of the polycation-ligand conjugate to the nucleic acid is less than about 5:1 (w:w).

54. The composition according to claim 51, wherein the ligand is a polypeptide reactive with a cell growth factor receptor.

55. The composition according to claim 54, wherein the ligand is a polypeptide reactive with a fibroblast growth factor (FGF) receptor.

56. The composition according to claim 51, wherein the excipient is selected from the group consisting of a zwitterion, an amorphous cryoprotectant, a crystalline bulking agent, and mixtures thereof.

57. The composition according to claim 51, wherein the excipient comprises a zwitterion, an amorphous cryoprotectant, and a crystalline bulking agent.

58. The composition according to claim 51, wherein the excipient comprises an amorphous cryoprotectant and a crystalline bulking agent.

59. The composition according to claim 51, wherein the excipient comprises at least one zwitterion selected from the group consisting of an amino acid, a polypeptide, and a biological buffer.

60. The composition according to claim 56, wherein the amorphous cryoprotectant is selected from the group consisting of a saccharide, a polyol, and a polypeptide.

61. The composition according to claim 56, wherein the crystalline bulking agent is selected from the group consisting of D-mannitol, trehalose, and dextran.

62. The composition according to claim 51, wherein the composition forms a plurality of particles and wherein the particles increase in size by less than one-fold during storage in a liquid medium for one week at about 2° C. to about 8° C.

63. A method of preparing a condensed nucleic acid comprising the steps of:
   a. admixing a nucleic acid and a polycation in a liquid medium to form an admixture;
   b. incubating the admixture under conditions in which the nucleic acid and the polycation condense to form a plurality of particles;
   c. lyophilizing the admixture to remove the liquid medium thereby producing a lyophile comprising particles; and
   d. reconstituting the lyophile with a predetermined volume of a reconstituting medium to form a reconstituted composition comprising a plurality of particles that increase in size less than one-fold during storage in the reconstituting liquid for one week at about 2° C. to about 8° C.

64. The method according to claim 63, wherein the average size of the particles in the reconstituted composition of step (d) is less than twice the average particle size of the particles in step (b).

65. The method according to claim 63, wherein the concentration of particles in the reconstituted composition of step (d) is greater than the concentration of particles in the composition prepared in step (b).

66. The method according to claim 63, further comprising the additional step of admixing an excipient into the liquid medium before step (c) and wherein the excipient is selected from the group consisting of a zwitterion, an amorphous cryoprotectant, a crystalline bulking agent, and mixtures thereof.

67. The method according to claim 63, further comprising the additional step of admixing an amorphous cryoprotectant into the liquid medium before step (c).

68. The method according to claim 67, further comprising the additional step of admixing a crystalline bulking agent into the liquid medium before step (c).

69. The method according to claim 67, further comprising the additional step of admixing a zwitterion into the liquid medium before step (c).

70. The method according to claim 67, further comprising the additional step of admixing an amorphous cryoprotectant, a crystalline bulking agent and a zwitterion into the liquid medium before step (c).

71. The method according to claim 67, further comprising the additional step of admixing an amorphous cryoprotectant into the liquid medium after step (b) and before step (c).

72. The method according to claim 67, further comprising the additional step of admixing a zwitterion into the liquid medium after step (b) and before step (c).

73. The method according to claim 63, further comprising the additional step of admixing an amorphous cryoprotectant and a zwitterion into the liquid medium after step (b) and before step (c).

74. The method according to claim 63, further comprising the additional step of admixing an amorphous cryoprotectant, a bulking agent and a zwitterion into the liquid medium after step (b) and before step (c).

75. The method according to claim 63, wherein the nucleic acid concentration in the admixture of step (b) is less than about 0.5 mg/mi.

76. The method according to claim 63, wherein the concentration of nucleic acid in the reconstituted composition of step (d) is less than about 20 mg/ml.

77. The method according to claim 63, wherein the polycation has a ligand attached thereto.

78. The method according to claim 63, wherein the particles in the reconstituted composition of step (d) have a hydrodynamic diameter of less than about 200 nm.

79. The method according to claim 63, wherein the particles have a hydrodynamic diameter less than about 100 mn.

80. The method according to claim 63, wherein the particles have a hydrodynamic diameter of less than about 80 nm.

81. The method according to claim 63, wherein the average size of the particles in the reconstituted composition of step (d) increases less than one fold during storage at about 2° C. to about 8° C. for one week.

82. A composition for the delivery of a nucleic acid to a mammalian cell prepared by the method according to claim 63.

* * * * *

UNITED STATES PATENT AND TRADEMARK OFFICE
CERTIFICATE OF CORRECTION

PATENT NO. : 6,251,599 B1
DATED : June 26, 2001
INVENTOR(S) : Xian Chen et al.

It is certified that error appears in the above-identified patent and that said Letters Patent is hereby corrected as shown below:

Column 33,
Lines 66 and 76, "wherein the lypophile" should read -- wherein the lyophile --.

Signed and Sealed this

Seventh Day of May, 2002

Attest:

Attesting Officer

JAMES E. ROGAN
*Director of the United States Patent and Trademark Office*